United States Patent [19]

Soto et al.

[11] Patent Number: 5,135,849
[45] Date of Patent: *Aug. 4, 1992

[54] IN-VITRO METHODS FOR IDENTIFYING COMPOSITIONS WHICH ARE AGONISTS AND ANTAGONISTS OF ANDROGENS

[75] Inventors: Ana M. Soto; Carlos Sonnenschein, both of Boston, Mass.

[73] Assignee: Trustees of Tufts College, Medford, Mass.

[*] Notice: The portion of the term of this patent subsequent to Aug. 22, 2006 has been disclaimed.

[21] Appl. No.: 339,800

[22] Filed: Apr. 18, 1989

Related U.S. Application Data

[63] Continuation of Ser. No. 853,240, Apr. 17, 1986, Pat. No. 4,859,585.

[51] Int. Cl.$^5$ ............................................. C12Q 1/02
[52] U.S. Cl. ..................................... 435/29; 435/948
[58] Field of Search ................................ 435/29, 948

[56] References Cited

U.S. PATENT DOCUMENTS 4,859,585  8/1989  Sonnenschein et al. ............... 435/29

OTHER PUBLICATIONS

Horoscewicz et al., *Biol. Abstr.,* 76, Abstr. No. 42757, 1983.
Noguchi et al., *Cancer Research,* 47, 263-268, 1987.
Stanley et al., *Cell,* 10, 35-44, 1977.

*Primary Examiner*—David A. Saunders
*Attorney, Agent, or Firm*—David Prashker

[57] ABSTRACT

The present invention provides general protocols by which a substance may be identified and characterized as an androgen agonist and/or an androgen antagonist. The described protocols are in-vitro methods which utilize androgen dependent cells in culture and a medium comprising an inhibitor endogenous to the sera of humans and animals which is able to prevent the proliferation of these cultured cells in-vitro. The methodology is rapid, reproducible, and accurate; and provides the major advantage of being able to test large numbers of unevaluated substances for their androgen agonistic and/or antagonistic properties as primary properties or secondary side-effects.

12 Claims, 7 Drawing Sheets

PANEL A: 5α-DHT (○—○), 3α-DIOL (●—●), 3β-DIOL (△—△) AND R1881 (▲—▲); PANEL B: 5α-DHT (○—○), ESTRADIOL-17α (△—△) ESTRADIOL-17β (●—●), ETHINYL ESTRADIOL (▲—▲) AND ORG 4333 (□—□); AND PANEL C: 5α-DHT (○—○) PROGESTERONE (●—●) AND R 5020 (△—△)

10% CDHuS - SUPPLEMENTED MEDIA WERE SUPPLEMENTED WITH:
(A) DHT (o—o), ANADRON (●—●), CYPROTERONE ACETATE (△—△);
AND MEDROXYPROGESTERONE ACETATE (▲—▲);
(B) DHT (o—o), FLUTAMIDE (●—●) AND HYDROXYFLUTAMIDE (△—△)

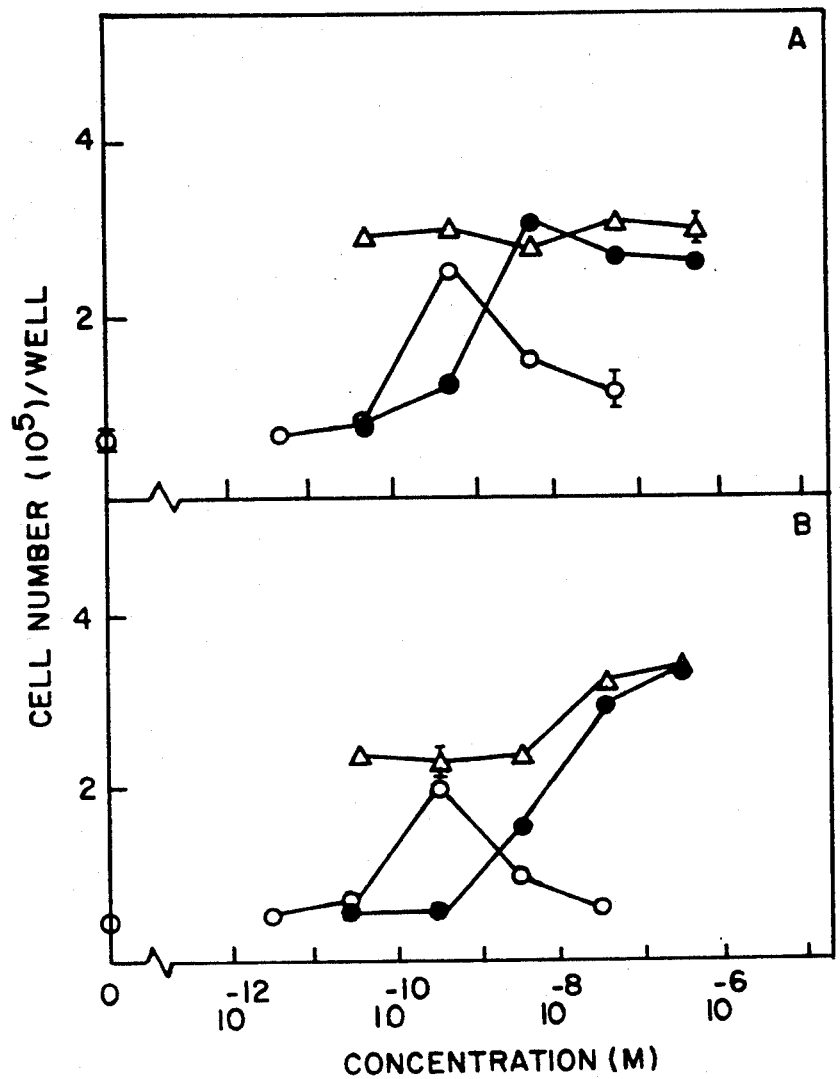

10% CDHuS - SUPPLEMENTED MEDIA AND EXPOSED TO:

(A) DHT (o—o), MEDROXYPROGESTERONE ACETATE (●—●), VARIABLE DOSES OF MEDROXYPROGESTERONE ACETATE ($3 \times 10^{-11}$ TO $3 \times 10^{-7}$ M)

(B) DHT (o—o), HYDROXYFLUTAMIDE ALONE (●—●), VARIABLE DOSES OF HYDROXYFLUTAMIDE ($3 \times 10^{-11}$ TO $3 \times 10^{-7}$ M) PLUS $3 \times 10^{-10}$ M DHT (△—△) AND VARIABLE DOSES OF DHT ($3 \times 10^{-12}$ TO $3 \times 10^{-8}$ M) AND $3 \times 10^{-8}$ M HYDROXYFLUTAMIDE (▲—▲)

FIG. 4

IN-VITRO METHODS FOR IDENTIFYING COMPOSITIONS WHICH ARE AGONISTS AND ANTAGONISTS OF ANDROGENS

FINANCIAL SUPPORT

The research for the invention was funded in part by the National Institutes of Health under Grant NIH C A13410.

CROSS-REFERENCE

This application is a Continuation-In-Part of application Ser. No. 853,240 filed Apr. 17, 1986, now U.S. Pat. No. 4,859,585, issued Aug. 22, 1989.

FIELD OF THE INVENTION

The present invention is concerned generally with methods for identifying chemical compositions whose pharmacological activities mimic or contradict the action of naturally occurring androgens; and is particularly directed to in-vitro protocols which will classify a variety of different pharmacologically active compositions as being either full or partial agonists and/or full or partial antagonists of androgens.

BACKGROUND OF THE INVENTION

Androgens constitute a group of 19-carbon steroid hormones that exert profound influence on the male genital tract and are involved with the development and maintenance of secondary male sex characteristics such as beard growth, deepening of the voice at puberty, muscle and bone development, body strength, and sexual drive. Androgens are synthesized in the male testis, in the female ovary, and in the adrenal cortex of both sexes. Once released into the blood circulation, these endogenous androgens serve both as hormones and as prohormones for the formation of two different classes of steroids: 5α-reduced androgens, which act as the intracellular mediators of most actions of the male sex hormones; and estrogens, which enhance some androgenic effects and block others.

Testosterone is the principal androgen secreted by the testis and is the main androgenic steroid in the plasma of males. In women, small amounts of testosterone are synthesized by the ovary and adrenals. Typically, testosterone is reduced at the 5α position into dihydrotestosterone, which serves as the intracellular mediator of most hormone actions. Although a variety of other naturally occurring androgens have been identified, these are generally weak in potency; and it is now generally believed that they are androgens only to the extent that they can be converted in-vivo to testosterone and/or dihydrotestosterone.

The major metabolites of androgens in urine are physiologically inactive either as free steroids or as water-soluble conjugates. These metabolites are predominantly etiocholanolone, a 5α-reduced metabolite of testosterone; and androsterone, a metabolite of dihydrotestosterone. It is now also recognized that testosterone (but not dihydrotestosterone can be aromatized into estradiol in a variety of extraglandular tissues, a pathway that accounts for most estrogen synthesis in men and postmenopausal women. The role, if any, of the approximately 50 micrograms of estradiol synthesized each day in normal men has never been defined. Nevertheless, the production of estradiol is considered a normal phenomenon. Experimental evidence suggests that estradiol affects the proliferation of male sex secondary organs; and that estradiol is necessary to induce prostate cancer in animal models. For a more detailed and comprehensive description of in-vivo synthesis of androgens, its metabolic pathways, intermediates, and reaction products, the following texts are recommended: *The Pharmacological Basis Of Therapeutics* (Goodman et al., editors), 7th edition, MacMillan Publishing Company, New York, 1985, pages 1440–1458; *Basic & Clinical Endocrinology* (Greenspan and Forsham, editors), 2nd edition, Lange Medical Publications, Los Altos, California, 1986.

The elucidation of the chemistry of androgens found in-vivo and the evaluation of androgenic potency for such compositions were and remain based on the use of specific in-vivo bioassays. The classical bioassay is based upon the growth of the comb of the capon, an assay developed by A. Butenandt and Tscherning, K. 8 *Z. Physiol.* 229:167 (1934)]. The determination of androgenic activity utilizing the growth response of the capon's comb was employed in the first isolation of androsterone, a metabolite of testosterone, from male urine [Butenandt, A., *Z. Angew. Chem.* 4:905–908 (1931)]. Subsequently, bioassays using live mammals in which the test depended upon inducing the growth of the seminal vesicles or ventral prostate of the castrated male were found to provide better correlations of activity and potency. These in-vivo mammalian bioassays were employed for the evaluation of testicular extracts [Loewe, S. and H.E. Voss, *Klin. Wochenschr.* 9:481–487 (1930)]; and for the isolation in crystalline form and elucidation of chemical structure for testosterone [David et al., *Hoppe Seylers Z. Physiol. Chem.* 233:281–282 (1935); Ruzicka, L. and A. Wettstein, *Helv. Chim. Acta* 18:1264–1275 (1935)]. Moreover, these in-vivo bioassays remain the most reliable methods known today by which to evaluate the androgenic potency of different chemical compositions.

In actual practice, these in-vivo animal tests measure the increase in wet weight of the ventral prostate or the seminal vesicles of castrated animals based upon the administration of androgenic hormones. It is now known that androgens induce cell proliferation, that is—an increase in the cell number (hyperplasia); an cause an enlargement of individual cell size (hypertrophy); and also cause the accumulation of water (water imbibition) and solutes in the extracellular space. Accordingly, it is recognized and appreciated that the total wet weight does not represent an appropriate estimate of only the proliferative action of hormone at all. In addition to these hormonal actions, androgens also subsequently inhibit the proliferation of their target cells in-vivo; it is noted that once the prostate and seminal vesicles of the castrated animal reach the cell number found in normal adult males during continued administration of testosterone, a plateau level in cell number is reached and no further cell proliferation is observed [N. Bruchovsky et al., *Vit & Horm.* 33:61–102 (1975)]. In sum, therefore, these in-vivo animal assays measure only the entire combination of all these diverse hormonal effects and cannot effectively measure only the proliferative capability alone.

In an effort to avoid using live animals and to diminish the variability of in-vivo assay methods, a variety of in-vitro tests have been proposed. These include: The assay of sex hormone-binding globulins; and specific radioimmunoassays sensitive for androgens [James et al., "Measurement Of Androgens In Biological Fluids", in *Androgens And Antiandrogens* (Maritini, L. and M. Motta, editors), Raven Press, New York, 1977, pages 19-35]. Similarly, the search for non-androgenic anabolic steroids has made use of in-vitro assays employing the growth of the kidney or levator ani muscle of castrated animals; and introduced in-vitro assays examining nitrogen excretion and the nitrogen-retaining effects of agents given to live animals on controlled diets. As recognized generally, none of these substitute in-vitro assays have been satisfactory.

It is also noteworthy that all the presently accepted assay techniques, whether performed in-vivo or in-vitro, are based upon a single common mechanism of action for all androgens as a class—including endogenous androgens; synthetically synthesized androgens; and other substances demonstrating the requisite ability to develop and maintain secondary male sex characteristics which is the classical definition and identifying trait of an androgen. The theory almost universally accepted today relies upon the assumption that androgenic effects can only be mediated by the interaction of androgens with intracellular androgen receptors present in the testis and accessory structures (epididymis, vas deferens, and seminal vesicles); the sebaceous glands; and the skeletal muscles. Potent androgens, such as testosterone or dihydrotestosterone, are said to bind to such a cytoplasmic protein receptor and to form a hormone-receptor complex intracellularly. This complex once formed then is said to be physically translocated into the nucleus of the cell where further binding of the complex at specific sites on the chromosomes is said to occur. This in turn is said to cause a general increase in protein synthesis and is said also to initiate new proliferation of the cells in-situ. Accordingly, the conventional mechanism of action for androgens as a class is that all the properties and known actions for androgens are mediated by a single class of cytoplasmic receptor protein; and that it is impossible to separate between the properties of new cell proliferation and new protein synthesis provided by an androgen because the mechanism of action is the same regardless of intended biological or clinical effects [Mainwaring, W.I.P., *Monogr. Endocrinol.* 10:1-178 (1977); Pardridge, W.M., *Endrocrin. Rev.* 103-123 (1981); *The Testis* (Burger, H. and D. DeKretser, editors), Raven Press, New York, 1981; Moguilewsky et al., in *Prostate Cancer*, Part A, Alan R. Liss, Inc., 1987, pp. 315-340].

With this conventional mechanism of action in mind, the recognized therapeutic uses for endogenous and synthetic androgens lie primarily in treating deficient endocrine function of the testis. In addition, some potent androgens have been utilized in treating a variety of other clinical disorders in the hope that their administration on non-genital tissues would also be beneficial. These other clinical conditions include: hypogonadism; improvements in nitrogen balance and muscle development, particularly via the use of anabolic steroids; the stimulation of erythropoiesis; hereditary angioneurotic edema; the management of growth retardation and short stature; carcinoma of the female breast; osteoporosis; and decreasing total plasma triglycerides and very low density lipoproteins in the blood.

Complementary to the use of known potent androgens has been the search for compounds which might actually inhibit or neutralize the action of androgens—the so-called "antiandrogens". The treatment of cancer of the prostate was clearly one of the earlier aims and goals for using such antiandrogens; however, the therapeutic uses of potent antagonists of androgens have been suggested for virilization in women, precocious puberty in boys, acne treatment, and satyriasis in adult men. There is also considerable interest in the potential use of such antiandrogens as male contraceptives. Substative progress along these lines, however, has been much less than might be hoped for.

Antiandrogens have been classified as steroidal (exemplified by cyproterone acetate and medroxyprogesterone acetate) and as non-steroidal [exemplified by flutamide and its metabolite, hydroxy-flutamide, and anandron (R23908); Raynaud and Ojasoo, *J. Ster. Biochem.* 25:811-833 (1986)]. Probably the best known and frequently employed potent steroidal antiandrogen is cyproterone acetate [Neri, R.O., *Adv. Sex Horm. Res.* 2:233-262 (1976);; Neumann, F., *Ir. J. Med. Sci.* 15:61-70 (1982)]. A fairly comprehensive listing of presently known antiandrogens can be found in *Prostate Cancer*, Part A, (Murphy, G.P. et al., editors), Alan R. Liss, New York, 1987; and Raynaud, J.P. and Ojasoo, T., *J. Ster. Biochem.* 25:811-833 (1986). The difficulty with these conventionally known compositions is that when these putative antiandrogens are given therapeutically, they may affect a variety of different endocrine organs such as the hypophysis, the adrenal cortex, and the testis indiscriminately and through these actions, these compositions may decrease plasma androgen levels. Note that true antiandrogens should impair only the effects of potent androgens rather than cause an actual decrease in androgen production and a reduction of plasma androgens. Unfortunately, the presently known antiandrogens appear not to discriminate between these vastly different properties and capabilities; and, accordingly, remain highly questionable in their abilities as true antiandrogens.

The difficulties of identifying and evaluating new compositions which are agonists and antagonists of androgens are generally recognized despite the variety and disparity of methods known to date. In-vivo methods have been generally difficult to perform in a consistent manner; and are open to independent biological variations which cannot be entirely controlled or eliminated. Conventionally available in-vitro systems have been at best indirect assessments or estimates of many different properties and parameters which are at best only somewhat correlatable with the potency and in-vivo activity of known androgens as a class. Equally limiting and restrictive is the continuing demand and reliance upon a generally acceptable single mechanism of action for androgenic compounds and antiandrogenic compositions—the pharmacological and biological effects for which must be tailored to conform and comply with an often contradictory and extremely complex series of cellular events inherently based on the existence and use of cytoplasmic receptor protein specific for these compositions. As can now be readily appreciated, there is a long standing and continuing need for reliable, accurate, and sensitive in-vitro assay protocols which will identify those pharmacologically active substances which are demonstratably potent as androgens and which will distinguish these from inhibitors or neutralizers of potent androgens, and from those substances which are completely quiescent with respect to the proliferative effect of androgens.

SUMMARY OF THE INVENTION

The present invention comprises in-vitro methods for identifying and characterizing a substance as an androgen agonist for and/or as an androgen antagonist against inducing the proliferation of androgen sensitive cells. The method for identifying an androgen agonist comprises the steps of obtaining a plurality of cells cultured in-vitro, these cells being androgen dependent for proliferation in-vivo; maintaining a known quantity of these cultured cells in a medium comprising a fluid and an inhibitor endogenous to the sera of humans or animals, this endogenous inhibitor being present in the medium at a concentration effective to prevent proliferation of the cells in-vitro; adding a test substance to the cultured cells and the maintaining medium to form a reaction mixture; incubating the reaction mixture for a preselected period of time; and determining the number of cultured cells in the incubated reaction mixture, a measurable increase in the number of cultured cells serving to identify the test substance as an androgen agonist.

The general method for identifying an androgen antagonist comprises the steps of obtaining a plurality of cells cultured in-vitro, these cells being androgen dependent for proliferation in-vivo; maintaining a known quantity of these cultured cells in a medium comprising a fluid and an inhibitor endogenous to the sera of humans or animals, the endogenous inhibitor being present in the medium at a concentration effective to prevent proliferation of the cells in-vitro; adding a test substance and an androgen to the cultured cells and the maintaining medium to form a reaction mixture; incubating the reaction mixture for a preselected period of time; and determining the number of cultured cells in the incubated reaction mixture, the failure of said cultured cells to measurably increase in number serving to identify the test substance as being an androgen antagonist.

Although each method comprising the invention may be performed to advantage individually and independently, it is preferred that both general methodologies be performed concurrently or sequentially in order to obtain the broader range of information and data about the substance being evaluated. In addition, the methodology is rapid, technically easy to perform, and provides meaningful data in a precisely controlled in-vitro assay environment.

DETAILED DESCRIPTION OF THE DRAWING

The present invention may be more easily and completely understood when taken in conjunction with the accompanying drawing, in which:

FIGS. 4A and 4B are graphs illustrating the absence of antagonistic effects for medroxyprogesterone and hydroxyflutamide following the Phase 2 protocol procedure;

DETAILED DESCRIPTION OF THE PREFERRED EMBODIMENTS

Figure 1:
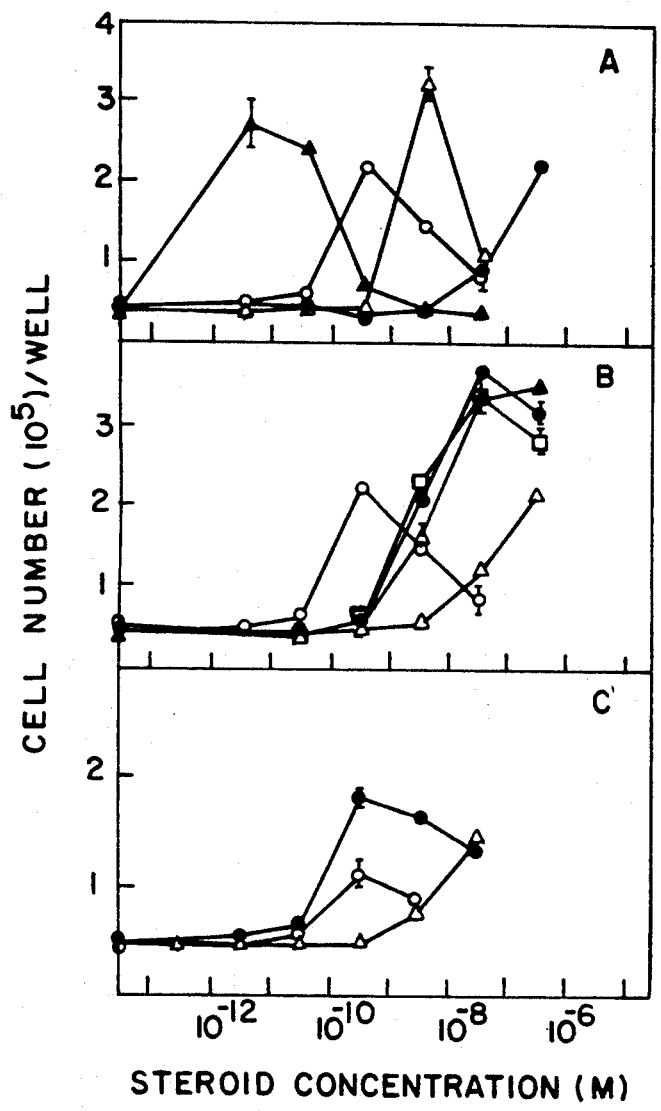
FIGS. 1A-1C are graphs illustrating the dose-response curves of androgens, progestins, and estrogens following the Phase 1 protocol procedure.

The present invention is a general, in-vitro test methodology which is used in alternative modes and provides distinct protocols for the identification and characterization of unknown substances for their capacity to serve as agonists and/or antagonists of endogenous androgens.

There are multiple major advantages provided by the methodologies comprising the present invention. These include:

1. The ability to identify previously available or newly synthesized compounds as androgen agonists and/or androgen antagonists in a verifiable and reproducible manner within a controlled in-vitro assay environment. The assay parameters and factors are predetermined and carefully prepared to lie within selected limits—thereby eliminating the effects of individual biological variation common to all in-vivo studies.

2. The capability to test statistically significant numbers of different substances over a relatively short period of time. Although the optimal time for each test is five to seven days in duration, each day's testing is performed in staggered series; accordingly, several hundred individual test samples can be prepared within one average working day and a different compound can be tested each day following in succession. Over a two week time period, at least five different days' testing can be empirically evaluated.

3. The means for reducing the present costs of testing are provided by each protocol of the present invention. In comparison with present in-vivo animal studies and their concomittant high cost per animal, their limited availability in numbers, and their inconvenience (housing, maintenance, and handling), the described in-vitro methods are very inexpensive to perform. Furthermore, in view of the major budget constraints now commonly in effect as a limiting factor in the realization of bringing a new therapeutic composition to market, the present invention offers a cost-effective procedure for evaluating the many presently synthesized compounds which were considered marginal and thus unlikely for ever being evaluated via in-vivo testing.

4. The means for correlating the pharmacological properties of the substance under test directly with its individual structural organization and chemical formulation. The protocols of the present invention are completely unlike the known in-vivo assay methods and do not rely upon the appearance of gross anatomical changes for results. Moreover, unlike any conventionally known in-vivo or in-vitro assays, the described protocols are not based upon the pre-existence of specific cellular androgen receptor proteins; do not require that androgens induce new protein synthesis; and do not require that an androgen-receptor protein complex be either formed or directly linked to new cell proliferation. The present invention, instead, permits the user to take into account the negative control mechanism of action; and with this context, empirically evaluates the individual physiological and/or pharmacological activity. Moreover, it allows a more detailed evaluation of the structure-function relationship of the test substance with regard to naturally occurring, serum-bourne inhibitors of cell proliferation.

As a result of the nature of the research and the historical development of the sex hormones in this art, a number of terms have come into common usage which are anachronistic misnomers at best, often misrepresentative, and frequently distortive in the worst instances. These terms include: "androgenic", "androgenicity", and "antiandrogen". Equally misfocused and misleading is the common practice of directly linking the ability of potent androgens to bind with its receptor protein intracellularly and to initiate new protein synthesis in a target cell with the distinctly different capability of the androgen to induce new cell proliferation. Contrary and in opposition to this common practice, the present invention relies and depends upon a complete separation of each capability individually and provides the means to evaluate each of them independently without any direct interdependence between them.

To avoid adding to the present state of confusion and miscommunication, and to enhance the ease and clarity of understanding for both the basis of the present invention and the major advance in this art which it represents, a set of strictly-adhered-to definitions and terminology will be employed herein. It will be expressly noted that the terms "androgenic" and "antiandrogen" have no well-defined meaning; and are conventionally used inconsistently and indiscriminately. Therefore, these terms will not be used in the description text which follows hereinafter. Instead, the following nomenclature, terminology, and definitions shall be used exclusively.

Androgens: A class of compounds including naturally occurring and synthetically made compositions which have a demonstrated ability to induce proliferation of specific cells and tissues in-vivo and in-vitro. Cells and tissues said to be androgen-dependent (or sensitive) are those cells and tissues which require one or more of the naturally occurring androgens to be present for the cells and tissues to proliferate in-vivo. Synthetic androgens mimic the characteristics of naturally occurring androgens in varying degree to induce proliferation of specific androgen-dependent cells, tissues, and organs in-vivo and in-vitro. As used herein, the ability of naturally occurring androgens and/or synthetic androgens either to initiate or to fail to initiate new protein synthesis within targeted cells and tissues is of no substantive consequence or meaning.

Naturally occurring androgens: The two most potent and naturally occurring (endogenous) androgens are: testosterone and dihydrotestosterone. Of these, dihydrotestosterone in the form of 5α-dihydrotestosterone is the most active pharmacologically and is the androgen of choice for use in the test methodologies comprising the present invention. A variety of other naturally occurring, but weaker, androgens are also known. These include: the testosterone precursor, androstenedione; the adrenal androgen, dehydroandrostenedione; and the metabolites 5α-androstene-3β,17β-diol, and androsterone.

Synthetic androgens: A class of compounds not occurring in nature which duplicate, emulate, or mimic the activity of endogenous androgens at least in some degree. These exogenous compounds include a variety of steroidal compositions exemplified by testosterone propionate (Testex); testosterone enanthate (Delatestryl); testosterone cypionate (Depotestosterone); methyltesterone (Metandren); fluoxymesterone (Halotestin); Danazol (Danocrine); R1881; and Mibolerone (DMNT). The pharmacological activities of these synthetic compositions often present dual and sometimes conflicting properties. For example, methyltestosterone is noted for its ability to mimic naturally occurring testosterone; however, methyltestosterone was the first of all 17α-alkyl substituted synthetic androgens found to cause cholestatic hepatitis. On the other hand, some synthetic androgens which mimic the potency of naturally occurring testosterone are also demonstrated to be potent anabolic steroids. In fact, all anabolic steroids known to date are individually able to mimic endogenous androgens in some degree.

Full or complete androgen agonist: A compound that either produces, emulates, or mimics the effect of naturally occurring endogenous androgens.

Partial androgen agonist: A compound that either produces, emulates, or mimics the effects of naturally occurring endogenous androgens in some meaningful degree but which is markedly inferior in activity and effect with respect to the results obtained with a full agonist even at the highest attainable concentration or dosage.

Full or complete androgen antagonist: A compound which completely inhibits or neutralizes the effect of a naturally occurring potent androgen when in the presence of or when administered concurrently with such an endogenous androgen.

Partial androgen antagonist: A compound which only partially neutralizes or inhibits the effect of a naturally occurring potent androgen when in contact with or administered concurrently with such an endogenous androgen, even at the highest attainable concentration or dosage.

For purposes of the present invention, it is the ability of naturally occurring androgens to induce the proliferation of their target cells and tissues through an indirect, negative control mechanism of action which is of primary value and interest. For this reason, all substances under assay are evaluated for proliferative activity only with respect to naturally occurring potent androgens as a single standard. The present invention is based upon and utilizes the empirical finding that human and/or animal serum and plasma contain a demonstrable endogenous inhibitor against proliferation of specific target cells, "androcolyone-I", which prevents the proliferation of androgen dependent cells and tissues in-vivo and in-vitro. This androgen inhibitor is analogous in function and use to the specific serum-bourne inhibitor now recognized for estrogen dependent cells as described in the following publications: Soto, A.M. and C. Sonnenschein, *Biochem. Biophys. Res. Comm.* 122:1097–1103 (1984); Soto, A..M. and Sonnenschein, & C., *J. Ster. Biochem.* 23:87–94 (1985); Soto et al., *Cancer Res.* 46:2271–2276 (1986); Soto, A.M. and C. Sonnenschein, *Endocrine Rev.* 8:44–52 (1987).

Each of the in-vitro methods for identification of androgen agonists and androgen antagonists makes use of the indirect-negative mechanism present in-vivo, in which androgens demonstrably cancel the effect of serum- or plasma-bourne specific inhibitors of cell proliferation. The use of this specific negative control mechanism of action within an in-vitro methodology for the evaluation and characterization of unknown or untested substances as agonists and/or antagonists of naturally occurring androgens is previously unknown and unappreciated in this art.

I. Preferred Formats

The present invention is preferably utilized as a combination of two different in-vitro methodologies performed concurrently or in sequence. One test methodology identifies a test substance as an androgen agonists—that is, a substance which duplicates or mimics the effects of naturally occurring androgens completely or partially. The second methodology evaluates the test substance as an androgen antagonists—that is, as having the ability to inhibit or neutralize the effect of a naturally occurring androgen when both are combined or administered concurrently. The individual methods used to identify an agonist and/or antagonist of androgens employ common cells, common reagents, and follow similar protocols in the main. For this reason, the constituents commonly shared and used in both methods, albeit for different purposes and goals, will be described first.

Cells

A single cell line of human prostate androgen-dependent cells (ATCC CRL 1740) in culture, the LNCaP line, has been empirically employed in the identification methods described herein [Horoszewicz et al., *Cancer Res.* 43:1809–1818 (1983)]. The LNCaP cell line is maintained by conventional tissue culture methods and media commonly available and used in the art, many of which are commercially prepared and sold. The sole essential requirement for the cells in culture, as demonstrated by the LNCaP cell line, is the need for a naturally occurring androgen to be present before the cells can proliferate in-vivo—that is, in their naturally occurring state within a living subject or host wherein the blood circulation functions normally.

The most desirable cell line for assay use at the present time is the LNCaP-FGC cell established from a metastatic supraclavicular lymph node which was removed from a 50 year old patient with a prostate adenocarcinoma [Horoszewicz et al., *Cancer Res.* 43 1809–1818 (1983)].

Insofar as is presently known, there are no other androgen-dependent cell lines yet available which demonstrate the essential characteristic of requiring an endogenous androgen in order to proliferate in-vivo. Nevertheless, it is fully expected that additional androgen-dependent cell lines will be developed from both human and animal sources in the foreseeable future using conventional techniques. For purposes of practicing the present invention, therefore, it is expected that any and all of these yet-to-be developed cell lines will also be suitable for use within the protocols described herein so long as they demonstrate the single, essential requirement—dependency upon the presence of a potent androgen for proliferation in-vivo. In addition, to choose among these foreseeable, newly isolated androgen-dependent cell lines as they become available for use, some preferred characteristics and criterion are given. In general, mammalian cell lines are deemed most desirable, with human derived cells being more preferred than cell lines derived from mice, rats, cattle, and the like. In addition, it is very desirable that the developed cell line be an abnormal or a tumor cell obtained ex-vivo or derived from tumor tissue excised from the living host and subsequently grown in-vitro as the fully cultured androgen-dependent cell line. These preferences are given merely as general aides and guidance to the user; the individual, however, may freely choose from the then available androgen-dependent cultured cell lines on any other basis as the conditions or desires of the user dictate.

The preferred LNCaP cells are maintained routinely in Dulbecco's modification of Eagle Medium (DME) purchased from GIBCo, Grand Island, NY and supplemented with 5% fetal bovine serum (FBS) [Sterile Systems, Logan, UT]. These cells are routinely grown in 75 and 250 cm$^2$ plastic flasks (Corning Plastics, Corning, NY). To test their proliferative rate and proliferation yields, LNCaP-FGC cells are seeded in 12-well plates (Costar, Cambridge, MA) in 5% FBS-supplemented DME for 48 to 72 hours so cells would attach to the plastic surface. Then, the seeding media is quickly changed to the maintaining media when performing the evaluation methods. At this time, because LNCaP cells attach loosely to the plastic surface every effort is taken not to disrupt them. For quantitation purposes, the cell lysing solution is added to the maintaining media in each well so nuclei from attached and floating cells would be counted For cell yield assays, media are not changed during the length of the assay's duration (5–7 days).

In addition, as the yet-to-be developed, androgen dependent cells come into existence as established cell lines, these can be employed similarly to the LNCaP cells. Prior to their use in the protocols of the present invention, each of these yet-to-be developed cell lines are expected to be routinely grown in 5% (v/v) fetal bovine serum (hereinafter "FBS") in Dulbecco's modification of Eagle's Medium (hereinafter "DME") in an atmosphere of 5% $CO_2$/95% air under saturating humidity at 37° C.

At the time of test, the chosen cell line, preferably the LNCaP cell, is introduced at the stated aliquot concentrations into the wells of multiwell plates (Costar 3512 plates, Cambridge, MA). The cell aliquot in each well is allowed to attach to the surface of the well for a period of 24–72 hours after which the seeding medium (5% FBS in DME) is removed and replaced by specific quantities of the maintaining medium used during the testing phases. Preferably, the fluid comprising the maintaining medium is phenol-red free DME supplemented with various concentrations of charcoal-dextran stripped human serum (hereinafter "CDHS"). The preference for CDHS is highlighted by the cell/serum homology; this assures the closest representation of equivalence to human testing without using human subjects.

Charcoal-Dextran Stripped Inhibitory Sera

Empirical data has shown that the specific inhibitor able to prevent proliferation of androgen-dependent cells and tissues in-vivo is serum (or plasma) bourne. This inhibitor, the "androcolyone-I" has been found not only in the blood (sera) of male and female humans; but also in the blood (sera) of bovines, horses, pigs, dogs, rats, and mice. The inhibitor is heat stable. For the previously stated reasons, it is preferred that heat-inactivated human sera (or plasma) be used routinely for the assay methodology.

In general, human heat-inactivated sera is more inhibitory than animal derived blood sera at volume/volume levels. The description which follows, therefore, is directed at obtaining and preparing sera from humans. It will be expressly understood, however, that a similar procedure may be usefully employed for the preparation of inhibitor-containing sera (or plasma) from any and all animal sources.

Venous blood is drawn from healthy human adult men and women. The blood is allowed to clot on sterile 50 milliliter (hereinafter "ml") plastic tubes for approximately four hours' duration. The sera are then clarified by centrifugation (3,000 rpm for ten minutes); subsequently "heat inactivated" (30 minutes at 56° C.); aliquoted into said volumes; and stored at—20° C. indefinitely for future use. When needed, the sera are thawed and stripped of endogenous androgens by extraction with 0.5% charcoal in the following manner.

A 0.5% charcoal (Norit A, acid washed, Sigma Corporation)—0.05% dextran T70 (Pharmacia Corporation, Piscataway, NJ) suspension is prepared. The charcoal-dextran aliquots, in volumes similar to the volume of the serum aliquots to be processed, are centrifuged at 3,000 rpm for 10 minutes to pack the charcoal into a pellet. The supernatants are aspirated to yield the formed charcoal pellet. Each serum aliquot is mixed with the charcoal pellet and maintained in suspension by means of a roller apparatus set at 3 cycles/minute at 37.5° C. for 60 minutes duration. The content of the tubes is spun down; and the supernatant is filtered through a 0.45 micron porous filter and then aliquoted. To monitor the extraction efficiency, comparable volumes of each sera are equilibrated for 16 hours at room temperature with $^3H$ radiolabelled estradiol or testosterone at $10^{-9}$ M and $10^{-8}$ M concentrations respectively, prior to charcoal extraction. It is found that 99% of the radiolabelled androgen is removed by this treatment. Charcoal-dextran stripped sera are used either immediately after stripping or are again frozen at $-20°$ C. until required for assay use.

Each of the prepared sera are combined with the charcoal pellets and are consequently stripped of endogenous androgens via this extraction method. Subsequent testing demonstrates that the endogenous inhibitor remains stable in the treated serum even after successive charcoal-dextran extractions.

Within the preferred protocols to identify agonists and antagonists of androgens, the CDHS is added to the DME in quantities sufficient to form a final concentration ranging from 40 to 2% by volume. This CDHS and DME in combination comprises the preferred maintaining medium for use in the protocols. The actual concentrations of endogenous inhibitor present in the CDHS thus are also diluted in concentration to a working range of between 40 to 2% of its original concentration in adult human serum.

Androgens

The androgens preferred for use with the methods of the present invention comprise the natural endogenous androgens, testosterone, and 5α-dihydrotestosterone. If desired, it is possible to utilize any of the wide variety of synthetically made androgens as the comparative basis. However, this latter approach is not preferred because of the wide range of steroidal and non-steroidal compositions which, although able to mimic the effect of endogenous androgens, also have been claimed to have antagonistic effects. The androgen of choice to be used within the in-vitro methods should be highly potent and be without antagonistic properties. The preferred androgen thus is 5α-dihydrotestosterone (hereinafter "5α-DHT"). Alternatively, testosterone itself can be employed. Both are recognized potent endogenous androgens.

The Preferred Protocols

It is most preferred that the present invention be performed as two test protocols or phases in order that a single substance under test be evaluated and identified in terms of its agonistic and antagonistic properties with respect to 5α-DHT. For ease and simplicity, the Phase 1 protocol identifies agonistic characteristics; in turn, the Phase 2 protocol identifies the antagonistic characteristics. Each test protocol will be described in detail.

Phase 1 Protocol to Identify Androgen Agonist Properties

This protocol measures the potential agonistic properties of the substance under test. All manipulations are to be carried out under sterile conditions using disposable plastic tissue culture multiwell plates with all manipulations preferrably being performed in a tissue culture hood.

1. The cell line of choice is the LNCaP-FGC cell culture, an androgen-sensitive prostate tumor cell line. The LNaP cell line is routinely grown in 5% fetal bovine serum—supplemented Dulbecco's modified Eagle minimal essential medium (hereinafter "5% FBS/DME"), at 37° C. in a 95% air—5% $CO_2$ atmosphere.

2. The cultured cells growing in 5% FBS/DME are harvested by treatment with trypsin (1:250)—EDTA (0.2%). The cells are detached by brief exposure to trypsin for about two minutes. To avoid excessive proteolysis, the reaction is quenched by addition of equal volumes of 5% FBS/DME. The resulting cell suspension is collected into a sterile centrifuge tube and resuspended by pipetting gently. The aliquots of this cell suspension thus obtained are dispersed by means of a Skatron dispenser into individual wells containing the seedling medium (1 ml of 5% FBS/DME per well) of a multiwell plate. Each final prepared suspension preferably contains 50,000 cells in a volume of 1.0 ml. It is desirable that the number of cells be counted and verified by means of a Coulter Counter (Coulter Electronics, Hialeah, FL).

The number of wells in each plate will correspond to the number of concentrations per test substances to be evaluated and thus is merely a question of choice or convenience to the user. Into each well, 25 microliter (hereinafter "ul") aliquots of the prepared cell suspension are added using a 1.0 ml syringe fitted with a 19 gauge needle attached to a repetitive Dunn pipetter (Skatron Dispenser). The microtiter plate is then gently shaken to avoid unequal cell distribution within each individual well. The seeded cells are then allowed to attach to the plastic surface of the well proper over a period of 24–72 hours' duration after which the fluid is changed to the experimental maintaining medium.

3 At the time of test, all the seeded cells in each well of the multiwell plate receive 10% heat inactivated—charcoal-dextran human stripped serum (CDHS) in DME at a volume of 0.9 ml per well. Although higher concentrations of CDHS may be utilized up to and including 40% concentrations, the 10% concentration is most preferred.

4 To those wells or plates designated as controls, 5α-DHT is added in a range of ever decreasing concentration. Preferably, a series of controls are prepared containing: no 5α-DHT (the negative control); as well as 5α-DHT concentrations of $3 \times 10^{-8}$ M; $3 \times 10^{-9}$ M; $3 \times 10^{-10}$ M; $3 \times 10^{-11}$ M; and $3 \times 10^{-12}$ M (the positive controls). Each of these respective concentrations of 5α-DHT are achieved by adding a 10X stock solution in a preferred total volume of 100 ul of DME. If desired, experimental controls having concentrations of 5α-DHT up to $10^{-5}$ M may be utilized to advantage. However, 5α-DHT causes maximum cellular proliferation at an optimum concentration of $3 \times 10^{-10}$ M. Concentrations of 5α-DHT above $3 \times 10^{-10}$ M result in progressively lower cell yields (see FIG. 1). For this reason, the preferred controls contain the described range of concentrations for 5α-DHT.

5. To the other prepared (seeded) wells, 100 ul of the test substance to be evaluated is added as a 10X stock solution to achieve final concentrations ranging from $10^{-5}$ M to at least $10^{-12}$ M. The substance under test is preferably prepared as a stock solution in ethanol, most preferrably as a $10^{-3}$ M solution. All dilutions from the stock preparation are made using DME. The ethanol concentration in the culture medium should be kept below 0.01% by volume. This preparative technique and precaution avoids the need to filter the various volumes of test substance to achieve sterility. This is particularly valuable because steroidal compositions are known to become adsorbed to the commercially obtained filter membranes used for sterilization. The addition of the test substance in appropriate concentrations to the cultured cells and the maintaining medium forms a series of individual reaction mixtures, each of which is varied only by the concentration of the test substance present in the well.

6. After the series of individual reaction mixtures are formed, all of the cultured cells under test in each well of the microtiter plate are incubated at 37° C. preferably in an atmosphere of 5% $CO_2$/95% air under saturating humidity. During this incubation time, it is desired and preferred that the cultured cells employed in the test be maintained in an atmosphere most advantageous for survival and growth of that cell line. The incubation period preferably is in the range of from 5 to 7 days' duration. The 5 day incubation period is considered optimal in order to allow sufficient proliferation of the cells serving as controls so that substantial differences in proliferation among the positive and negative controls and the test cell suspensions may exist on a regular and recurring basis.

7 After the preferred incubation period of 5 to 7 days has elapsed, the cells from each test and control well are collectively harvested and each well is counted separately. Cells are harvested using a lysing solution such as 10% zapoglobin (Coulter Electronics, Hialeah, FL) that disrupts the plasma membranes while leaving the cell nuclei intact without clumping A preferred lysing solution comprises 10% zapoglobin, 0.5% Triton X 100, 2 mM mg $Cl_2$, and 15 mM NaCl in 5 mM phosphate buffer, pH 7.4. The nuclei suspensions are individually counted using an efficient cell counter (Coulter Counter Apparatus, model ZF) and the cell numbers per well (mean±standard deviation) recorded.

8. To obtain reproducible, accurate, and reliable data consistently using this protocol, a series of quality assurance measures should be employed. Under preferred conditions, the cell number per well obtained from the control containing $3 \times 10^{-10}$ M 5α-DHT should preferably be about 3-5 fold higher than the cell numbers obtained in those reaction mixtures which did not contain any 5α-DHT. These goals are achieved using the optimal 5-7 day incubation period. In addition, a separate quality control performance estimate should be obtained by measuring the proliferation rate of a separate $5 \times 10^4$ cell innoculum in a 10% CDHS with and without 5α-DHT in a $3 \times 10^{-10}$ M concentration. For this innoculum, cells are harvested every 24-48 hours (preferably as triplicate samples) until the entire 5-7 day incubation period expires. A good estimate of the proliferation rate is the mean generation time, "$t_D$". $t_D$ is calculated from the equation $\alpha = 1/t \times \ln C_t/C_o$, where $C_o$ is the initial cell number, $C_t$ is the cell number at time$-t$, and $\alpha$ is the instantaneous cell proliferation constant ($t_D$ is the value $\ln C_t/C_o$ x would have when $C_t = 2C_o$) "$t_D$" is expressed in time units, i.e., hr. The slopes of the different growth curves are calculated by fitting the experimental data to a straight line by regression analysis of the pairs ln cell numbers/time. $t_o$ is defined as the moment at which the seeding medium is replaced by the maintaining medium. In these conditions, the doubling time ($t_D$) of LNCaP cells is about 40 hrs for the cultures in 10% CDHS+$3 \times 10^{-10}$ M 5α-DHT, and about 300 hrs for the control (androgenless) cultures (see FIG. 2).

9 The interpretation of the empirically derived data in which the number of cultured cells present in each of the incubated reaction mixtures is determined, is directly based on the premise that a measurable increase in the number of cultured cells in those reaction mixtures containing the substance under test identifies the substance as an androgen agonist. In other words, the substance under test has overtly demonstrated the ability to interact with the endogenous inhibitor present in charcoal-dextran stripped human serum; and has empirically neutralized the effects of the endogenous inhibitor in such degree that the cells can proliferate. The ability to interact and neutralize the effect of the endogenous inhibitor present in the CDHS either in part or in complete degree also serves to identify the substance under test as a partial agonist or as a full agonist. The differences are illustrated by the data presented in FIG. 1.

Figure 2:
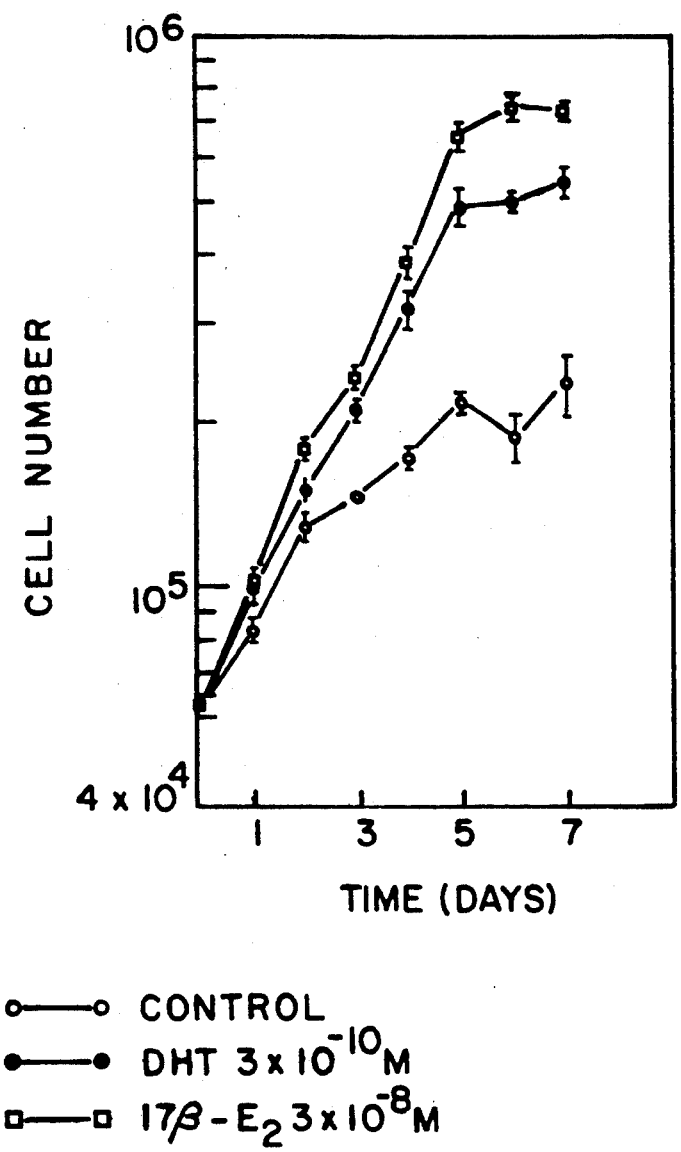
FIG. 2 is a graph illustrating the LNCaP cells grown in the presence and absence of sex steroids.

As is revealed by the graphs of FIGS. 1 and 2, the basis of evaluation is the demonstrated ability of 5α-DHT to induce proliferation of the LNCaP cell in in-vitro in the presence of 10% CDHS in comparison to the degree of cell proliferation empirically provided by LNCaP cells in the control wells. A test substance evaluated in a manner similar to 5α-DHT in this protocol will thus demonstrate one of three distinctly different phenomena and capabilities: activity as a full or complete agonist which behaves in a manner similar to 5α-DHT although the maximum proliferative effect may occur at a use concentration above or below the maximal growth effect induced by 5α-DHT at the $3 \times 10^{-10}$ M concentration; activity as a partial agonist which shows some ability by the test substance to induce a measurable cell proliferation in comparison to the number of cells maintained in the control wells which do not meaningfull proliferate at all, but this measurable increase never approaches the numerical values (total cell number) provided by an endogenous androgen such as 5α-DHT; or activity as a quiescent composition which provides no substantial or meaningful increase in the number of cultured cells over those numbers yielded by the negative control and accordingly is said to have no ability to induce or initiate cell proliferation under the test circumstances of the protocol. In this manner, by empirically comparing the ability of the test substance either to initiate or to fail to initiate new cell proliferation in comparison to positive and negative controls under the described test circumstances, such agonistic characteristics as are inherent in the substance under test are revealed and evaluated on a comparative basis with an endogenous androgen such as 5α-DHT.

Phase 2 Protocol for Identification of Androgen Antagonistic Properties

This test protocol identifies and measures (on a comparative basis) the antagonistic properties of uncharacterized substances when concurrently combined with a potent androgen within the confines of a prepared cell culture. The protocol is similar to the Phase 1 protocol in: the selection of a cell line (preferably LNCaP cells) for culture in-vitro which is demonstrably androgen dependent for proliferation in-vivo; the preparation of aliquots of cells which are subsequently seeded into a plurality of wells in a microtiter plate; the use of 5% FBS in DME as a seeding medium until the time of test; and the use of 10% CDHS in DME as the preferred maintaining media sufficient to provide the endogenous inhibitor at a concentration effective to prevent proliferation in-vitro of the seeded cells in each test well.

Accordingly, steps 1 through 3 are again performed as stated earlier within the protocol of Phase 1, the full description of each individual step not being reproduced again here. In essence, $5 \times 10^4$ cultured cells are seeded into each individual well, test, and control. The culture medium is changed to 10% CDHS in DME (the maintaining medium); and a series of combinations containing 5α-DHT and test substance added to the cultured cells to form a series of individual reaction mixtures, preferably as follows:

(a) no androgen or test substance added (negative control);

(b) $3 \times 10^{-10}$ M 5α-DHT and $3 \times 10^{-4}$ M test substance;

(c) $3 \times 10^{-10}$ M 5α-DHT and $3 \times 10^{-5}$ M test substance;

(d) $3 \times 10^{-10}$ M 5α-DHT and $3 \times 10^{-6}$ M test substance;

(e) $3 \times 10^{-10}$ M 5α-DHT and $3 \times 10^{-7}$ M test substance; and (f) $3 \times 10^{-10}$ M 5α-DHT and $3 \times 10^{-8}$ M test substance.

In a separate multiwell plate, a variety of 5α-DHT concentrations without any test substance are added to equally seeded wells; this series of reaction mixtures is to serve as positive controls in which the optimal effect of 5α-DHT is tested. In addition, another multiwell plate is similarly prepared to contain a variety of concentrations of the test substance alone without any 5α-DHT whatsoever. This provides a direct comparative basis for the resulting data.

It will be noted that varying concentrations of the test substance ranging from approximately $10^{-4}$ to $10^{-10}$ M are uniformly combined with the most effective proliferation concentration of 5α-DHT, $3 \times 10^{-10}$ M. This concentration of 5α-DHT has been empirically found to be most effective to induce cell poliferation in the majority of instances; however, the use concentration of the chosen androgen in this Phase 2 protocol may be varied to meet the individual user's needs or desires. It is required only that one uniform concentration of 5α-DHT (or other naturally occurring or synthetic androgen) be employed in sufficient but not exceedingly higher concentration than that required for maximal cell proliferation in combination with varying concentrations of the substance under test. For this reason, the preferred concentrations for the substance to be evaluated are as described above; nevertheless, the specified test concentrations may be increased or decreased in accordance with the individual needs or desires of the user.

Subsequent to adding the prepared concentrations of the test substance and the 5α-DHT to each of the wells containing aliquots of cells in known quantity to form a series of individual reaction mixtures, each of the reaction mixtures is incubated in the manner identical to that described in the Phase 1 protocol for a preferred time period of between 5 and 7 days. As noted before, the true incubation time may be varied; nevertheless it is preferred that the incubation period be not less than 5 days routinely.

After the chosen incubation period has elapsed, the number of cells in each of the individual wells, test and control, are determined in the manner identical to that described for Phase 1 testing. The cells are harvested with a lysing solution that disrupts the plasma membranes leaving the cell nuclei intact without clumping. The individual nuclei suspensions from each of the wells are then counted separately using a Coulter Counter and the cell number per well (mean±standard deviation) are calculated accordingly. By definition, an androgen antagonist is a substance which when combined with an androgen results in a reduction of cell poliferation (the final number of cells after incubation) in comparison with the final cell count obtained by using the androgen alone. The empirically obtained final cell counts from any test series should be interpreted in accordance with the results graphically plotted in FIGS. 3 and 4.

As seen in the graph of FIGS. 1 and 2, the LNCaP-FGC cultured cells incubated in-vitro in media containing CDHS alone fail to proliferate in comparison to the positive controls. Clearly, the negative controls containing no 5α-DHT or no test substance whatsoever, effectively maintain only a reduced number of cells when compared with yields from 5α-DHT containing cultures. In this manner, the endogenous inhibitor present in the 10% CDHS is shown to inhibit the proliferation of the LNCaP cells in culture thereby providing a substantially constant number throughout the test period. In comparison, the positive controls comprising 10% CDHS and 5α-DHT without any test substance induce cell proliferation and provide a much higher number of cells at the end of the test period—a number of cells about 2-5 times greater than the negative control in a 7 day assay. In comparison to both these positive and negative controls, the test substance combined with 5α-DHT may demonstrate either a small decrease in total cell number; or a major, substantive decrease in cell number with respect to the positive controls. A large, substantive decrease in cell number identifies the action of a full or complete antagonist; such a substance is able to reduce the cell proliferation rate in a range from the maximal rate induced by the androgen to the minimal level comparable to the negative controls containing no androgen whatsoever. Correspondingly, a partial antagonist will decrease the cell growth rate to intermediate values; that is, a cell number lower than the positive control yields containing androgen alone yet higher than those cell numbers provided by the negative controls containing no androgen whatsoever. It will be recognized (by the manipulative steps comprising the Phase 2 protocol and by interpretation of the resulting empirical data) that a test substance able to suppress the demonstrated ability of 5α-DHT to neutralize the effects of the endogenous inhibitor present in the serum is therefore an empirically demonstrated androgen antagonist. The degree to which the substance suppresses the proliferative effects of the 5α-DHT upon the cells in culture will then identify and characterize that test substance as being either a complete antagonist or merely a partial antagonist.

It should be noted that these antagonistic characteristics are separate and distinct from any agonistic properties which may have been identified previously using the Phase 1 protocol. The co-existence of agonistic and antagonistic properties in a single substance is not an unusual event; and is not in any way contradictory or evidence of artifact in the test methodology. To the contrary, the co-existence of such properties within a single substance which then identifies that substance as being a partial or complete agonist concurrently with being a partial or complete antagonist of androgens is a phenomenon which has many parallels in this art. This dual capability, therefore, is and remains a realistic and factual possibility even though it is expected that the majority of tested substances will demonstrate but one activity as either an agonist or an antagonist of androgens.

To illustrate the accuracy and reproducibility of both the Phase 1 and Phase 2 protocols, a series of experiments was performed evaluating the variety of pharmacologically active substances each of which is known in the scientific literature. The substances evaluated as test samples include the following: estradiol-17β (Calbiochem, Richmond, CA); 5α-dihydrotestosterone, 5β-dihydrotestosterone, testosterone, progesterone, pregnenolone, 5α-androstene, 3α,17β-diol (3α-diol), 5α-androstene, 3β-17β-diol (3β-diol), hydrocortisone, and diethylstilbestrol (DES) (Steraloids, Keene, NH); Moxestrol and R1881 (Roussell-UCLAF, Romainville, France); R5020 (New England Nuclear Company, Boston, MA); Org 4333 (11β-chloromethyl estradiol) (Organon, Oss, The Netherlands); Mibolerone (7α,17α-dimethyl-19-nortestosterone) or "DMNT" (provided by Dr. A. Traish, Boston University School of Medicine); Epidermal Growth Factor (Collaborative Research, Lexington, MA, Lot No. 88-1341); and Creative Biomolecules Inc., Holliston, MA, Lot No. 055-A); and Insulin (Lot No. 615-075-256; Eli LIlly Company, Indianapolis, IN).

Estradiol is estra-1,3,5(10)-triene-3,17-diol [U.S. Pat. Nos. 2,096,744; 2,225,419; and 2,361,847]. Moxestrol is 11β-methoxy-19-nor-17a-1,3,5(10)-trien-20-yne-3,17-diol [U.S. Pat. No. 3,579,5450]. R5020 is 17βmethyl-,21-methyl-19-nor-pregna-4,9-diene-3,10-dione. Org 4333 is 11β-chloromethyl estradiol having clear estrogenic properties. R1881 is said to be 17β-hydroxy-17α-methyl-estra-4,9,11-trien-3-one by its manufacturer [Roussel-UCLAF, Paris, France]. Anandron (R23908) is 5,5-dimethyl-3-(4-nitro-3-(trifluoromethyl)-phenyl)-2,4-imidasolidinedione. Progesterone is a hormone secreted by the corpus luteum during the latter half of the menstrual cycle [U.S. Patent Nos. 2,379,832; 2,232,438; 2,314,185]. Each of these compositions were evaluated using the protocols described earlier for Phase 1 and Phase 2 tests. The results are presented in Table I below.

TABLE I

| COMPOUND | OPTIMAL TEST CONC. | PHASE 1 CELL COUNT | OPTIMAL TEST CONC. | PHASE II CELL COUNT | CHARACTERISTICS | INTENDED USE |
| --- | --- | --- | --- | --- | --- | --- |
| no addition | N.D. | $5 \times 10^4$ | N.D. | N.D. | N.D. | N.D. |
| 5α-DHT | $3 \times 10^{-10}$M | $2.5 \times 10^5$ | N.D. | N.D. | full agonist | agonist |
| 5β-DHT | $3 \times 10^{-8}$M | $2.5 \times 10^5$ | N.D. | N.D. | full agonist | agonist |
| testosterone | $3 \times 10^{-10}$M | $2.6 \times 10^5$ | N.D. | N.D. | full agonist | agonist |
| 3α-diol | $3 \times 10^{-7}$M | $2.5 \times 10^5$ | N.D. | N.D. | full agonist | agonist |
| 3β-diol | $3 \times 10^{-9}$M | $3.5 \times 10^5$ | N.D. | N.D. | full agonist | agonist |
| R1881 | $3 \times 10^{-12}$M | $2.5 \times 10^5$ | N.D. | N.D. | full agonist | agonist |
| mibolerone | $3 \times 10^{-12}$M | $2.5 \times 10^5$ | N.D. | N.D. | full agonist | agonist |
| estradiol 17β | $3 \times 10^{-8}$M | $4.0 \times 10^5$ | $3 \times 10^{-6}$M* | $4.0 \times 10^5$ | full agonist | antagonist |
| Org 4333 | $3 \times 10^{-8}$M | $4.0 \times 10^5$ | $3 \times 10^{-6}$M* | $4.0 \times 10^5$ | full agonist | antagonist |
| DES | ** | $5 \times 10^4$ | $3 \times 10^{-5}$M | $5 \times 10^4$ | full antagonist | antagonist |
| R2858 | ** | $5 \times 10^4$ | N.D. | N.D. | N.D. | antagonist |
| progesterone | $3 \times 10^{-10}$M | $4 \times 10^5$ | $3 \times 10^{-6}$M* | $4.0 \times 10^5$ | full agonist | antagonist |
| pregnenolone | $3 \times 10^{-8}$M | $3.9 \times 10^5$ | $3 \times 10^{-6}$M* | $3.9 \times 10^5$ | full agonist | antagonist |
| R5020 | $3 \times 10^{-8}$M | $4.0 \times 10^5$ | $3 \times 10^{-6}$M* | $4.0 \times 10^5$ | full agonist | antagonist |
| cyproterone acetate | $3 \times 10^{-8}$M | $4.1 \times 10^5$ | $3 \times 10^{-6}$M* | $4.1 \times 10^5$ | full agonist | antagonist |
| medroxy progesterone | $3 \times 10^{-9}$M | $4.0 \times 10^5$ | $3 \times 10^{-6}$M* | $4.0 \times 10^5$ | full agonist | antagonist |
| flutamide | ** | $5 \times 10^4$ | $3 \times 10^{-6}$M* | $4.0 \times 10^5$ | quiescent | antagonist |
| hydroxyflutamide | $3 \times 10^{-8}$M | $3.9 \times 10^5$ | $3 \times 10^{-6}$M* | $4.0 \times 10^5$ | full agonist | antagonist |
| anandron | $3 \times 10^{-8}$M | $4.0 \times 10^5$ | $3 \times 10^{-6}$M* | $4.0 \times 10^5$ | full agonist | antagonist |
| hydrocortisone | $3 \times 10^{-6}$M* | $5 \times 10^4$ | $3 \times 10^{-6}$M* | $5 \times 10^4$ | quiescent | antagonist |
| epidermal growth factor | 100 ng/ml | $5 \times 10^4$ | 100 ng/ml | $5 \times 10^4$ | quiescent | agonist |
| insulin | 100 ng/ml | $5 \times 10^4$ | 100 ng/ml | $5 \times 10^4$ | quiescent | agonist |

*maximal concentrated tested
**not active from $10^{-4}$ to $10^{-10}$M in Phase I
N.D. = no data It will be recognized that the empirical results are expressed as the final cell number obtained per well. The optimal concentration reported in Table I is the smallest concentration at which a maximal effect is detected, be it agonistic or antagonistic. Note that estradiol-17β, Org 4333, progesterone, R5020 and R1881 are each full agonists and demonstrate no antagonistic activity. In comparison, DES, IPP, and DPM show no agonistic activity at all but each is a full antagonist. Lastly, epidermal growth factor, insulin, flutamide, and hydrocortisone individually not active either as an agonist nor an antagonist, and for this reason are said to be quiescent.

It will be also recognized and appreciated that the characteristics identified for some the better known substances identified in Table I correspond to the various reports in the published literature regarding their conventionally known pharmacological characteristics. There are also some major surprises in the results of Table I, particularly as concerns estrogens and progestins as a class. By these empirical data, the ability of the present invention to accurately identify and distinguish between androgen agonists and androgen antagonists over a wide variety of substances is thus deemed to be unequivocally demonstrated.

II. Alternative Protocol Formats

As a practical matter, it should be recognized that the empirical results presented in Table I are based on the use of 10% CDHS prepared as described earlier herein. While it is theoretically possible to use 100% serum taken from humans or animals which has been adsorbed with charcoal-dextran, this is deemed impractical because such concentrated serum must be dialyzed to equilibrium against the fluid comprising the maintaining medium (preferably DME) to provide the nutrients and vitamins necessary for cell survival and multiplication during the incubation period of the test protocol. The 10% concentration of serum is preferred because this concentration provides consistent results and is much more economical than higher concentrations. Other CDHS concentrations up to 40% provide comparable results depending upon the sensitivity of the androgen-dependent cells in culture to the endogenous inhibitor in the serum; accordingly, the control values for those cells unable to proliferate are usually fewer in number when higher concentrations of CDHS are used, but this is not a significant factor so long as consistency of CDHS concentration chosen is maintained throughout the test methodology as a whole.

Alternatives to the Use of CDHS

Functional equivalents of CDHS in the maintaining medium may be employed in either Phase 1 and/or Phase 2 protocols freely as desired. The maintaining medium used in the test protocols is required to contain only two essential components; a fluid carrier (preferably DME) containing a requisite amount of nutrients, vitamins, salts, and the like to maintain the cell culture in a healthy, viable state; and a measurable concentration of an inhibitor endogenous to the serum of adult male and female humans and animals (primarily mammals) which is present in the fluid at a concentration effect to prevent the proliferation of the cells in-vitro. Both essential requirements are satisfied by the use of CDHS in more than 2% final concentration by volume. Alternatively, the maintaining medium may comprise any of the well known natural or synthetic preparations now available for the maintenance of cells in culture in combination with a predetermined quantity of concentrated, semi-purified, proteinaceous inhibitor which has been isolated from the plasma of adult humans

Protocol For Isolation Of Semi-Purified Androcolyone-I Inhibitor Able To Prevent Proliferation Of Androgen-Dependent Cells In-Vitro 1 Source: It is most preferred that outdated frozen plasma from adult humans be used. The plasma is not to be kept at 4° C. for more than 24 hours from the time it was drawn until the moment it is utilized in the purification protocol.

This precaution is taken to avoid degradation of the inhibitor by the serine proteases present in plasma. Serum may be employed in lieu of plasma if desired; however, outdated plasma is preferred because of its lesser cost.

2. Removal of coagulation factors: To the plasma sample maintained at 4° C., 5$\alpha$-DHT is added at a concentration of 100 picograms ($10^{-12}$ grams) per ml of plasma. To this mixture 1.0 M sodium citrate solution is added until a total volume concentration of 15 mM is obtained. To this total volume 1.0 M benzamidine is added until a final concentration of 5.0 mM is achieved. Subsequently, a 1.0 M $BaCl_2$ solution is added very slowly in sufficient quantity to achieve a final volume concentration of 80 mM in the fluid mixture. With the addition of $BaCl_2$ solution, a precipitate is formed which is stirred very gently to form a suspension. The reaction mixture is then placed in a container having an air-tight closure and positioned on a roller apparatus (Bellco Co., Vineland, NJ), and rotated for approximately 60 minutes at 4° C. Subsequently, the reaction mixture is centrifuged at 3,000 x gravity for 10 minutes to form a supernatant and a precipitant layer. After separating the fractions, the precipitant is discarded and the supernatant fraction chromatographed through Cibacron-blue agarose using conventionally known methods.

3. Chromatography: The purpose of this separation step is to remove albumin and estrocolyone. Cibacron-blue agarose (Pierce Chemical Co.) with an albumin binding capacity of 18 mg/ml gel is packed into a glass column. A short, broad column is preferred (diameter 2.6 cm, height 10 cm). The column is equilibrated with start buffer (25 mM tris-HCl, pH 7.0, containing 1 mM benzamidine). 20 ml of the $BaCl_2$ supernatant are applied to the column and eluted with start buffer This "breakthrough" fraction contains 50% of the androcolyone activity, 20% of the total plasma protein, and is mainly free of estrocolyone and albumin.

The adsorbed proteins are eluted with 2 M NaCl, 25 mM tris-HCl, pH 7.0, containing 1 mM benzamidine. This fraction contains albumin, estrocolyone, 50% of the androcolyone, and 80% of the total plasma proteins.

The "breakthrough" fraction is concentrated by ultrafiltration using a low protein binding membrane (Amicon 4M30) and dialysed against a buffer suitable for use in tissue culture, such as 25 mM Hepes buffer containing 100 mM NaCl, pH 7.4. The preferred ratio of inhibitor to dialysate fluid should be in the order of 1:50 by volume. In the preferred method, the dialysis step is performed with two changes of Hepes—NaCl buffer.

This method of preparation results in a 2.5 to 5 fold purification with a 50% yield of androcolyone-I. It should be noted that the inhibitory protein may degrade over time; accordingly, the inhibitor is preferably kept concentrated; 100 mM NaCl and 5 mM benzamidine are added; and the resulting preparation is frozen at $-80°$ C. until the time of use. This preparation must then be dialized as indicated above.

Assay to Determine the Potency of the Concentrated Androcolyne-I Inhibitor

The potency of the androcolyone-I isolated from human serum is defined in activity units. An activity unit is defined as that amount of purified androcolyone-I required in 1.0 ml of medium to inhibit one doubling of a $5 \times 10^4$ cell innoculum (the time required for a cell concentration to double in quantity) at the end of a 5 calendar day period. To determine the potency of any preparation comprising purified inhibitor, the following measurements should be performed, preferably in duplicate using simultaneously seeded wells Procedure I: Determination of the standard dose-response curve to different concentrations of CDHS in combination with varying concentrations of androgen such as (a) no 5α-DHT and (b) $3 \times 10^{-10}$ M 5α-DHT for a period of 5 days.

Procedure II: Determination of the dose-response curve to different concentrations of Cibacron-blue purified inhibitor preparations which have been added to DME containing 100 ng/ml of porcine insulin and 2 ug/ml of iron-charged transferrin (IT), in combination with varying concentrations of 5α-DHT such as (a) no 5α-DHT and (b) $3 \times 10^{-10}$ M 5α-DHT.

To perform Procedures I and II, innocula comprising $5 \times 10^4$ cells in 5% FBS are seeded into the wells of a multiwell plate. 48 hours later, the medium is changed: 1.0 ml per well of 1%, 2%, 5%, and 10% CDHS respectively (preferably as duplicate samples) for Procedure I; and 1.0 ml per well of different concentrations of partially purified inhibitor preparation in iT medium for Procedure II. All cell cultures are then harvested and counted on the 5th day of the test period in accordance with the methods described for the Phase 1 and 2 protocols.

From the empirically obtained cell count data, the ratio between 5α-DHT treated and 5α-DHT free cultures for each serum or inhibitor preparation is determined. This determination is made as follows:

1. The number of cells in existence on Day 5 of the test are taken from the series of samples comprising Procedures I and II respectively. A unit of androcolyone-I activity is defined as the amount needed to generate a 5α-DHT positive:5α-DHT negative ratio of 2; i.e., to inhibit one doubling in a 120 hour time period when the innoculum size is about $5 \times 10^4$ cells and the total medium volume is 1.0 ml.

2. A comparison of the total cell number at each inhibitor concentration, in the presence [(b) series] and absence [(a) series] of 5α-DHT may now be made. The comparison establishes whether or not the preparation contains an active inhibitor which is able to be neutralized by 5α-DHT; and whether or not spurious toxic materials are present in the preparation. In the latter instance, the action of the inhibitor is not reversed by endogenous estrogens.

III. The Underlying Mechanism of Action For The Phase 1 And Phase 2 Protocols The methods of the present invention are radically different and completely separate from conventionally known theories and assay methods which rely upon the presence of intracellular androgen-specific receptor sites to provide and account for both new cell proliferation and new protein synthesis by androgen-dependent cells. The conventional premise and theory relies upon testosterone as the primary molecule for initiation of both protein synthesis and cell proliferation. Under normal conditions, the conventional theory assumes that free testosterone enters the target cells and undergoes 5α reduction to 5α-dihydrotestosterone (5α-DHT), which in turn becomes bound to a specific receptor protein within the cell and forms a 5α-DHT/receptor protein complex. This 5α-DHT/receptor protein complex is then said to translocate into the nucleus of the cell. Once within the nucleus, the receptor/5α-DHT complex is said to bind to chromatin at specific binding sites on the chromosomes and initiates nucleic acid transcription. New messenger RNA is synthesized, chemically modified, and exported from the nucleus to the cytoplasm of the cell where ribosomes translate the mRNA into new proteins that have a recognized "androgenic" effect on the cell—that is, new protein synthesis and new cell growth/proliferation. The twin phenomena of new protein synthesis and new cell proliferation are each said to be the result of a single mechanism of action and the same series of intracellular events, each of which is expressly conditioned on the presence and active participation of androgen-specific receptor proteins within the target cells. For a more detailed and comprehensive description of this conventional theory and the molecular events said to be caused by the formation of the receptor protein/5α-DHT complex intracellularly, the following publications may be consulted: Liao, S. and S. Fang, *Vitam. Horm.* 27:17–90 (1969); Walsh et al., *N. Engl. J. Med.* 291:944–949 (1974); Mainwaring, W.I.P. (editor), *Monogr. Endocrinol.* 10:1–178 (1977); Griffin, J.E. and J.D. Wilson, *N. Engl. J. Med.* 302:198–209 (1980); Griffin et al., *Am. J. Physiol.* 243:E81–E87 (1982). See also: *Androgens And Antiandrogens* (Martini, L. and M. Motta, editors), Raven Press, New York, 1988; Endocrinology (L. DeGroot, editor), Grune & Stratton, 1979, Chapter 106; *Basic & Clinical Endocrinology*, Second Edition (Greenspan, F.S. and P.H. Forsham, editors), Lange Medical Publications, Los Altos, California, 1986, pages 449–450; and *The Pharmacological Basis Of Therapeutics*, Seventh Edition (Goodman, Gilman, Rall, and Murad, editors), MacMillan Publishing Company, New York, 1985, pages 1440–1458.

Evidence Of The Negative Control Mechanism Of Action For All Proliferation

Figure 5:
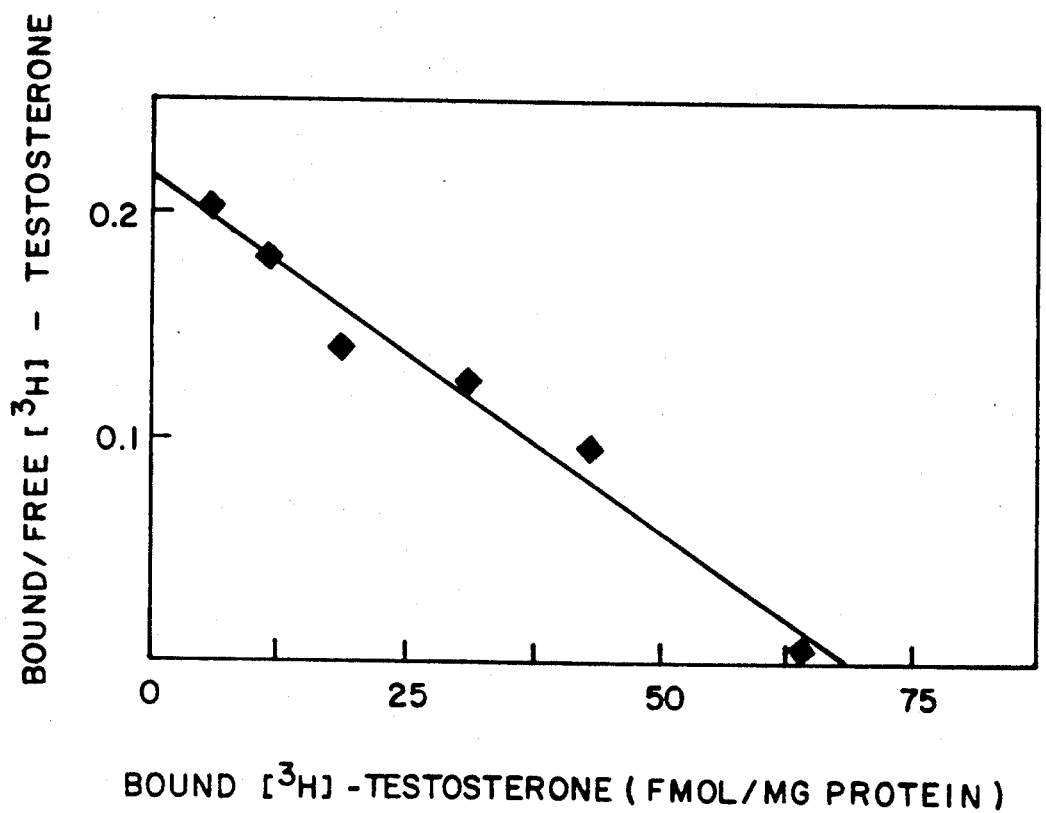
FIG. 5 is a graph illustrating the presence of specific androgen receptors in LNCaP cells.

To empirically demonstrate these different and divergent capabilities (control of cell proliferation vs. initiation of new protein synthesis), a series of investigations using the LNCaP cell line was undertaken. LNCaP cells have been reported in the literature to contain androgen receptor proteins [Horoszewicz et al., *Cancer Res.* 43:1809–1818 (1983)]. Recent experiments have confirmed the presence of an intracellular androgen binding protein with about 40,000 active binding sites per LNCaP cell. Moreover, the concentration of binding sites was about 68 fmoles/mg of receptor protein; and the $K_d$ of the receptor protein 5α-DHT complex was empirically found to be about $3 \times 10^{-9}$ M. This data is graphically shown by FIG. 5.

In addition, measurements of androgen-specific receptor protein and binding affinities with respect to a broad range of different steroidal and non-steroidal compositions was conducted as seen in Tables II and III infra.

The methods of the present invention have nothing in common with the conventional theory and mechanism of action based on the intracellular receptor protein complex. To the contrary, the Phase 1 and Phase 2 protocols described herein require and rely upon the presence and effect of androcolyone-I which exerts an anti-proliferative effect when in reactive contact with androgen-dependent cells and tissues. This inhibitor molecule is endogenous in the blood of humans and animals and does not bind to or otherwise react with the specific receptor proteins found intracellularly; but instead binds to the androgen-dependent cell at other cell sites to exert an anti-proliferative effect over the reproduction of these cells. This, in essence, is the negative control theory and mechanism of action [Soto, A.M. and C. Sonnenschein, *Endocr. Rev.* 8:44–52

(1987)] which is the very basis and foundation of the assay protocols to identify agonists and antagonists of endogenous androgens. Not only is the sequence of events requiring the presence and physiological effects of a discrete inhibitory molecule able to prevent cell proliferation markedly different and unrelated to the conventional view, but the negative control mechanism of action demands and requires recognition that the capability to initiate or prohibit cell proliferation is a fundamentally independent and discrete property completely separate and distinct from the cell's ability to initiate new protein synthesis.

Evidence empirically supporting this theory and mechanism of action is provided by an experimental series evaluating the Relative Binding Affinities (RBA's) in comparison to the proliferative potency.

"Relative Binding Affinity Experiments"

Materials and Methods

Steroids: Labelled steroids $^3$H-testosterone (S.A. - 3.1 TBq/mmol), $^3$H-estradiol-17$\beta$ (S.A. - 3.8 TBq/mmol), and $^3$H-R5020 (S.A. - 3.2 TBq/mmol) were purchased from New England Nuclear, Boston, MA.

Steroid receptors measurement: The presence of intracellular sex steroid binding proteins was investigated in whole cell extracts as well as in intact cells. Cytosolic and nuclear extracts were obtained after centrifugation (105,000 g, 45 min.) of a sonicated cellular suspension in TKE buffer (10 mM Tris, 500 mM KCl, 0.5 mM EDTA, pH 7.4). Aliquots of this extract were incubated for 18 hours at 4° C. with increasing concentrations ($2\times10^-$ M to $2\times10^{-8}$ M) of labelled steroids, with and without a 200-fold excess of the corresponding unlabelled steroid. Bound and free fractions were separated by dextran-coated charcoal adsorption. Intact cells grown in monolayer culture were assayed for specific steroid binding [Olea-Serrano et al., Eur. J. Cancer Clin. Oncol. 21:965-973 (1983)]. Briefly, the cells were incubated in 12-well plates during 50 minutes at 37° C. in DME containing the labelled steroid with and without excess of cold competitor. The range of concentrations used was the same as that in the cytosolic-nuclear extract assay. Previously, it has been demonstrated that the specific uptake of labelled steroids in these cells reaches plateau during the first 25 minutes of incubation. The intracellular radioactivity was extracted with ethanol after ice-cold PBS washing. In both types of experiments, Scatchard analysis of the saturation data was used to quantify the maximal binding capacity (Bmax) and the affinity parameters (dissociation constant, Kd) using the SCAFIT program [Munson et al., Anal. Biochem. 107:220-239 (1980)].

Cytosol-nuclear extracts were used to study competition for androgen receptors. Aliquots were incubated with $6\times10^{-9}$ M $^3$H-testosterone and variable concentrations of cold competitors (testosterone, 5$\alpha$-DHT, 3$\alpha$-diol, 3$\beta$-diol, mibolerone, R1881, estradiol-17$\beta$, estrone, estriol, ethinyl estradiol, DES, Org 4333, Moxestrol, progesterone, pregnenolone, and R5020) ranging from $5\times10^{-10}$ M to $5\times10^{-6}$ M. The assay was carried out as described above for the receptor assay. The relative binding affinity (RBA) was calculated from the equation:

RBA = testosterone ($I_{50}$)/test competitor ($I_{50}$)

that is, the ratio between the concentration of unlabelled testosterone and that of the competitor that inhibits 50% of the $^3$H-testosterone bound to the androgen receptor.

The results of these experiments are summarized by the data of Table II below.

TABLE II

COMPARISON BETWEEN RELATIVE BINDING AFFINITIES (RBA) TO THE ANDROGEN RECEPTOR AND PROLIFERATION POTENCIES OF DIVERSE STEROIDAL AND NON-STEROIDAL COMPOUNDS ON LNCaP CELLS

| COMPOUND | RBA[a] | RELATIVE PROLIFERATIVE POTENCY[b] |
|---|---|---|
| 5$\alpha$-DHT | 100 | 1.0 |
| 3$\alpha$-diol | 1.2 | 0.001 |
| 3$\beta$-diol | 14 | 0.1 |
| R1881 | 200 | 100 |
| Mibolerone | 15 | 100 |
| Estradiol-17$\beta$ | 0.9 | 0.01 |
| Estrone | 0.1 | —[c] |
| Estriol | <0.01 | — |
| Ethinyl estradiol | 1.4 | 0.01 |
| R2858 | <0.01 | — |
| Org 4333 | 1.2 | 0.01 |
| DES | <0.01 | — |
| Progesterone | 19 | 1.0 |
| Pregnenolone | <0.01 | 0.01 |
| R5020 | 11 | 0.01 |

[a]The relative binding affinity was calculated as indicated previously.
[b]The relative potency was the ratio between the concentration of testosterone and agonist necessary to elicit maximal cell yield for a 5 × 10$^4$ cell inoculum grown in CDHS for 8 days.
[c]No proliferative potency at the range of concentrations tested.

As shown, Table II compares the RBA and the proliferative potency of the compounds tested. $^3$H-E$_2$ binding was displaced by androgens and progestagens. DES and moxestrol, which bind to estrogen receptor present in estrogen-sensitive cells, did not compete with $^3$H-E$_2$ binding. These observations, as well as the absence of immunoreaction with monoclonal antibodies against human estrogen receptor (not shown) indicate that no estrogen receptor is present in these cells; this empirical showing also confirms data of others [Berns et al., The Prostate 9:247-259 (1986)]. R5020 binding was also displaced by androgens and estrogens with RBAs comparable to those observed when competition between $^3$H testosterone and progestagens was measured. These observations indicate that the steroid binding activity seems to represent androgen receptor.

While a good correlation between relative binding affinities and proliferative potency was established for some of the compounds tested, R1881 and mibolerone were more potent to induce cell proliferation than predicted by their respective RBAs. In addition, both progesterone and pregnenolone were more potent inducers of cell proliferation than predicted by their RBAs; pregnenolone displayed the most extreme lack of correlation between its RBA (<0.01%) and its proliferative potency (1%) when compared with 5$\alpha$-DHT values.

The data given above are incompatible with the direct and indirect positive hypotheses relying upon specific androgen receptor proteins intracellularly. On the other hand, these data are very compatible with and are empirical evidence for the direct and indirect negative hypotheses. According to our indirect negative hypothesis: androgens, estrogens, and progestagens induce cell proliferation by neutralizing a serum-borne specific inhibitor of androgen-sensitive cell proliferation (androcolyone-I). The interaction of androcolyone-I with sex steroids appears to be direct, i.e., it does not require hormone interaction with the intracellular androgen receptor. This represents compelling arguments for the unique mechanism of action for the Phase 1 and Phase 2 protocols.

Other evidence directly bearing on the parameter and performance of the methodology comprising the present invention is also provided below. The data and conclusions provided are supplementary to and evidence of the variety of embodiments useful and operative within the limits of the protocols.

Proliferation Rate of LNCaP Cells

The population doubling time of LNCaP cells was 40 hours when $3 \times 10^{-10}$ M 5α-DHT was added to 10% charcoal-dextran stripped human sera supplemented medium (FIG. 2). The inhibitory effect of CD human sera was not instantaneous; at the end of 3 to 4 days the population increase was halted and remained stable for up to 30 days without media changes. That these cells were then still viable is suggested by increased cell proliferation rates when $3 \times 10^{-10}$ M 5α-DHT was added 30 days after being in 10% CDHS (not shown). The proliferation rate of LNCaP cells growing in the presence of 5α-DHT was significantly faster than that of the control (minus 5α-DHT). Estradiol-17β showed a slightly shorter population doubling time. It appears that estradiol-17β allows for an additional population doubling over which is 5α-DHT influenced (see FIG. 2).

Serum Concentration Effects On Proliferation Yields

Figure 6A:
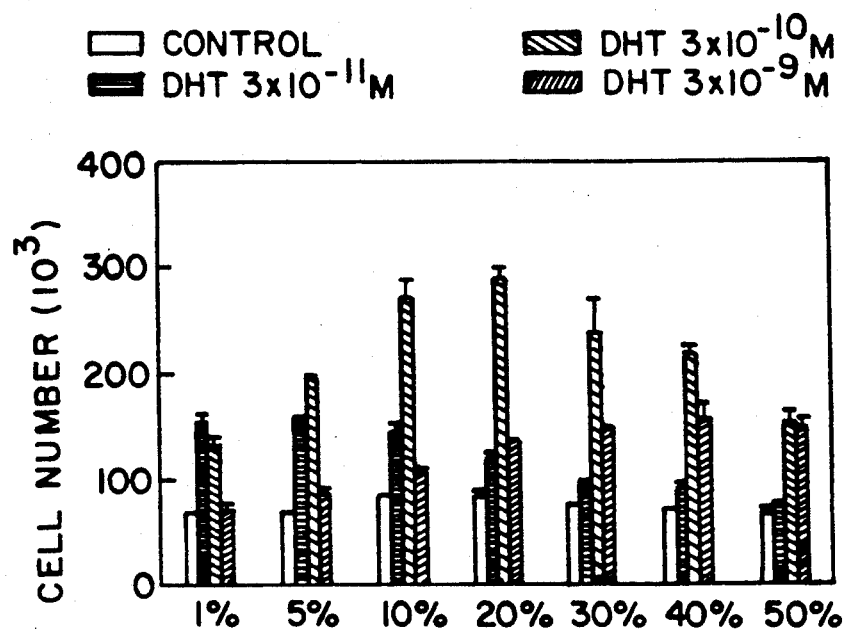
FIGS. 6A and 6B are graphs illustrating the effects of serum concentration on the proliferation of LNCaP cells when grown in media supplemented with 1 to 50% DCHuS.
Figure 6B:
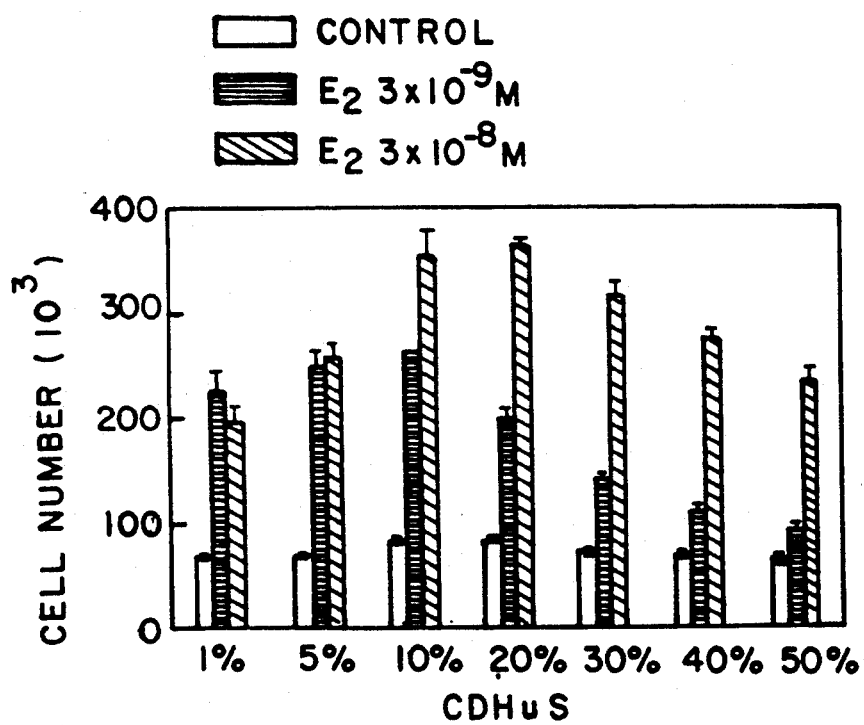

Absolute yields of cells varied according to the serum and sex hormone concentrations used and are graphically represented by FIGS. 6a and 6b. The proliferative effect of 5α-DHT appeared to be influenced by the serum concentration in the media; lower 5α-DHT concentrations ($3 \times 10^{-11}$ M) were necessary to cancel the inhibitory effect of low CD human serum supplemented media (1% to 5%). Higher 5α-DHT concentrations ($3 \times 10^{-10}$ M) were needed to cancel the inhibitory effect of high CD human serum supplemented media (10 to 50%). In addition, lower serum concentrations generated lower yields when compared with higher serum concentrations in experiments seeded and harvested simultaneously. A comparable pattern was obtained with estradiol-17β (FIG. 6b).

Effect Of Putative Growth Factors And Growth Inhibitors

Figure 7A:
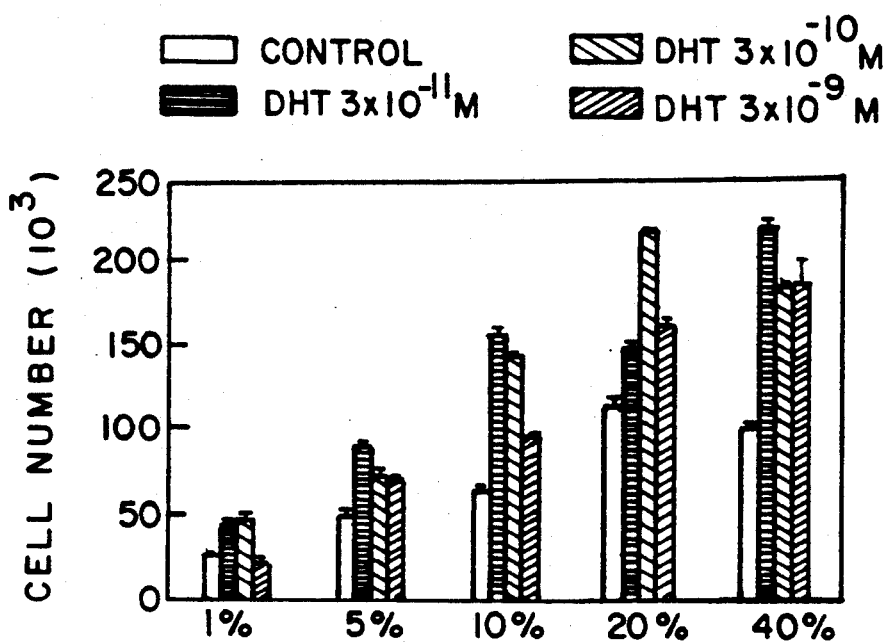
FIGS. 7A and 7B are graphs illustrating the effect of serum concentration in the seeding media for LNCaP cell proliferation.
Figure 7B:
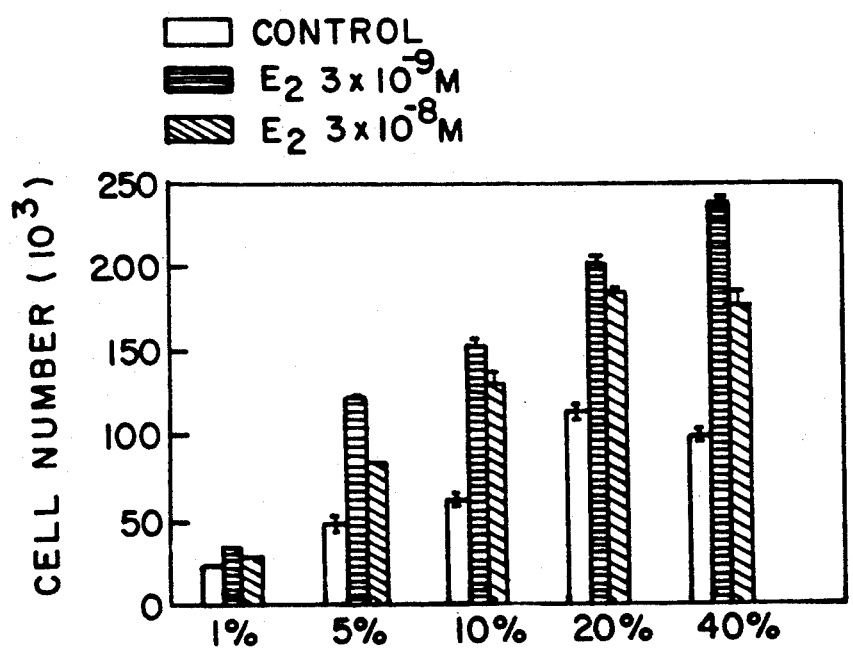

The testing of proliferation yields under putative serumless conditions revealed valuable information. As described above, cells were kept for 48 hours in 5% FBS such that a sufficient number of cells would become attached to the plastic surface. Cells seeded and kept for 48 hours in media supplemented with increasing concentrations of FBS (from 1 to 40%) showed a significantly different cell yield when challenged to proliferate in IET-supplemented DME; a direct positive correlation could be established between the serum concentration in the seeding media and the cell yield achieved in DME plus IET as shown by FIG. 7. When cells were seeded in 1% FBS the difference between cell yields of controls and sex hormone supplemented cultures were less significant than those recorded when cells were seeded in 5% or higher FBS concentrations.

IV. Other Applications And Information Provided By The Protocols

A. The protocols comprising the present invention can also be employed to provide comparative data regarding the relative potency of androgen agonists once the previously uncharacterized substance has been initially evaluated and empirically demonstrated to be an androgen agonist as such. For example, direct comparison assays showed about a 2 fold higher proliferation of LNCaP cells under similar test conditions when $3 \times 10^{-8}$ M estradiol-17β was used than when cultured in the presence of $3 \times 10^{-10}$ M 5α-DHT (the optimal concentration for proliferation). This is illustrated by the data of FIGS. 1 and 2.

Moreover, while testosterone showed a proliferative pattern similar to that obtained with 5α-DHT (Table I), 3α-androstenediol was found to be 1,000 fold less potent than 5α-DHT; and 3α-androstenediol was revealed to be 10 fold less potent than 5α-DHT (FIG. 1).

In addition, 19-nor-testosterone was 10 fold more potent than the cell yields provided by 5α-DHT (not shown). Similarly, the synthetic androgens R1881 (FIG. 1) and mibolerone (not shown) were 100 times more potent than 5α-DHT. Similarly, progesterone and R5020 were effective and potent androgen agonists as illustrated by FIG. 1 and Table II.

B. Another major application and result is the ability to properly evaluate and categorize the so-called "antiandrogens" in a reproducible and accurate manner. By eliminating the need for androgen antagonistic properties to be the result of binding with specific cytoplasmic receptor proteins in the target cells, the property of neutralizing the cell proliferative capability of potent androgens can be assessed directly; and, for the first time, the true attributes of the "antiandrogens" can be ascertained. This application is illustrated by the data presented by Table III and FIG. 3.

TABLE III

COMPARISON BETWEEN RELATIVE BINDING AFFINITY (RBA) TO THE ANDROGEN RECEPTOR EXTRACTED FROM LNCaP AND RELATIVE PROLIFERATION POTENCIES (RPP) OF STEROIDAL AND NON-STEROIDAL "ANTIANDROGENS"

| COMPOUND | RBA[a] | RPP[b] |
|---|---|---|
| Testosterone | 1 | 1 |
| Cyproterone acetate | 0.02 | 0.01 |
| Medroxyprogesterone acetate | 0.006 | 0.1 |
| Flutamide | <0.0001 | —[c] |
| Hydroxyflutamide | 0.004 | 0.01 |
| Anandron | 0.002 | 0.01 |

[a] The relative binding affinity was calculated as indicated in Materials and Methods.
[b] The relative potency was the ratio between the concentration of DHT and putative antagonist necessary to elicit maximal cell yield for a $10^5$ cell inoculum grown in CDHS for 7 days.
[c] No proliferative potency at the range of concentrations tested.

Figure 3:
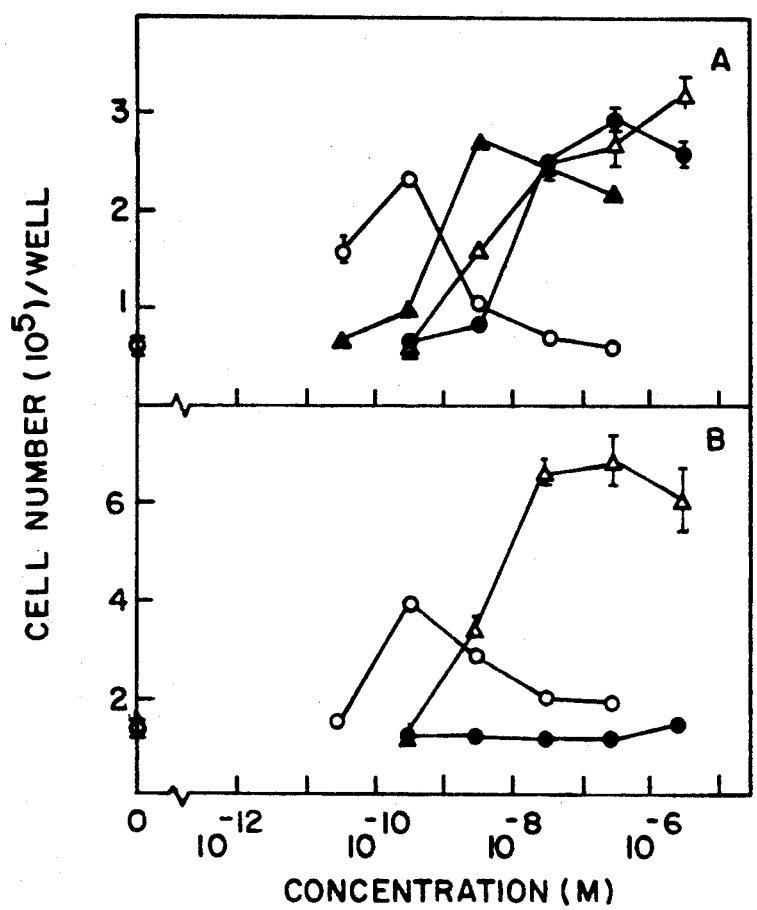
FIGS. 3A and 3B are graphs illustrating the agonistic properties of putative antiandrogens following the Phase 1 protocol procedure.

The data of Table III empirically demonstrates and evidences the value of the Phase 1 and Phase 2 protocols to identify agonists and antagonists by endogenous androgens. Two steroidal "antiandrogens" have been tested: cyproterone and medroxyprogesterone acetates. These are progestin derivatives with glucocorticoid and putative antiestrogenic and antiandrogenic activities [Tremblay, D., et al., *Prostate Cancer, Part A*, 1987, A.R. Liss, NY, pp. 341-350; Mowskowicz, I., et al., *Endocrinology* 95:1589-1599 (1974)]. FIGS. 3 and 4 and Table III indicate that the separate addition of these compounds to CDHS-supplemented media resulted in a significant increase in cell yields when compared with controls. Moreover, when both DHT and these steroidal "antiandrogens" were simultaneously administered to these cells: (a) a synergistic pattern evolved in the presence of $3\times10^{-10}$ M5α-DHT; (b) the "shut-off" mechanism triggered by $3\times10^{-8}$ M5α-DHT prevailed over the proliferative effect of "antiandrogens"; and (c) only when the ratio "antiandrogen" 5α-DHT was 100 to 1,000-fold, the "shut-off" effect was partially reversed resulting in an increased proliferative yield. Regardless of the mechanisms involved, the data clearly show increased LNCaP cell yields when adding "antiandrogens" to high levels of 5α-DHT in culture conditions.

Three non-steroidal "antiandrogens" were also studied: (i) flutamide, devoid of activity "in culture" (FIG. 3); (ii) hydroxyflutamide [Koch, H. *Drugs Today* 20:561-574 (1984)]; and (iii) a structural analog obtained by cyclisation of flutamide, anandron [Raynaud, J.P. and Ojasoo, T., *J. Ster. Biochem.* 25:811-833 (1986)]. These "antiandrogens" were chosen because of their inclusion in many standard protocols for the treatment of prostate cancer patients [Grayhack, J.T., et al., *Cancer* 60:589-601 (1987)]. Medroxyprogesterone was the most effective "anti-androgen" in increasing the proliferation yields of LNCaP cells, showing maximal effect at $3\times10^{-9}$ M and higher Cyproterone acetate, hydroxyflutamide, and anandron at $3\times10^{-8}$ M also increased cell yields at values consistently above those obtained with DHT alone; these higher yields were comparable to those obtained with $3\times10^{-8}$ M estradiol-17β and $3\times10^{-10}$ M progesterone (see FIGS. 1 and 3). Therefore, no significant differences between steroidal and nonsteroidal "antiandrogens" were observed in their proliferative patterns when tested in 10% CDHS. It is worth recalling that these LNCaP cells have androgen receptors (FIG. 5) but lack estrogen and progesterone receptors.

Within the context of the negative hypotheses, we interpret these results as follows: (a) the "antiandrogens" tested in this study interact with the plasma-borne specific inhibitors of the proliferation of these cells cancelling their effect (first step of the two-step mechanism); and (b) a relationship between "antiandrogens" and androgen receptors could be inferred from the interaction between $3\times10^{-6}$ M "antiandrogen" and $3\times10^{-8}$ M 5α-DHT (a concentration that triggers the "shut-off" effect) added simultaneously to these LNCaP cells. However, the net result of this tripartite interaction (5α-DHT-"antiandrogen"-androgen receptor) was a significant increase in the proliferation yield probably as a result of interference by "antiandrogens" on the 5α-DHT-androgen receptor interaction by mechanisms not fully understood; we submit that this latter interaction mediates the triggering of the "shut-off" response (second step of the two-step mechanism of androgen action on cell proliferation). Through both mechanisms, "anti-androgens" would promote the proliferation of human prostate cells that behave like LNCaP cells in culture.

Regardless of which working hypotheses one subscribes to, the clearcut proliferative response of these human prostate tumor cells to the administration of putative anti-androgens in a milieu that is designed to mimic as much as possible the real life microenvironment (human cells-human serum) represents a remarkable and troubling paradox. To resolve this paradox, one should entertain the possibility that: (a) the beneficial effects attributed to these compounds, if any, are not due to direct interaction with their perceived tumor target cells; (b) a more careful assessment of the data on their effectiveness may show a less significant or nill therapeutic values, a proposition advanced by others [Trachtenberg, *J. Urologic Clinics Of North America* 14:685-692 (1987)]; and/or (c) additional data may indeed suggest that these "antiandrogens" do impair the proliferation yield of prostate tumor cell populations having properties other than those described for LNCaP cells.

The present invention is not to be restricted in form nor limited in scope except by the claims appended hereto.

What we claim is:

1. An in-vitro method for identifying a substance of interest as an in-vivo androgen agonist, said method comprising the steps of:
    obtaining a plurality of cells consisting of LNCaP FGC (ATCC Accession No. CRL 1740) cultured in-vitro, said cells being androgen dependent for proliferation in-vivo;
    maintaining a known quantity of said cultured cells in a maintaining medium without androgens, said maintaining medium comprising a fluid and an inhibitor of androgen dependent call proliferation which is endogenous to the serum of humans or animals, said endogenous inhibitor being present in said maintaining medium at a concentration effective to prevent proliferation of said cells in-vitro in the absence of an androgen;
    adding the substance of interest to said cultured cells in said maintaining medium to form a reaction mixture;
    incubating said reaction mixture for a preselected time period; and
    determining the number of cultured cells in said incubated reaction mixture, a measurable increase in the number of cultured cells identifying the substance of interest as an androgen agonist.

2. An in-vitro method for identifying a substance of interest an in-vivo androgen agonist, said method comprising the steps of:
    obtaining a plurality of cells consisting of LNCaP. FGC (ATCC Accession No. CRL 1740) cultured in-vitro, said cells being androgen dependent for proliferation in-vivo;
    maintaining a known quantity of said cultured cells in a maintaining medium without androgens, said maintaining medium comprising a fluid and an inhibitor of androgen dependent cell proliferation which is endogenous to the serum of humans or animals, said endogenous inhibitor being present in said maintaining medium at a concentration effective to prevent proliferation of said cells in vitro in the absence of an androgen;
    adding the substance of interest and an androgen to said cultured cells in said maintaining medium to form a reaction mixture;
    incubating said reaction mixture for a preselected time period; and
    determining the number of cultured cells in said incubated reaction mixture, the failure of said cultured cells to maximally increase in number identifying the substance of interest as an androgen agonist.

3. An in-vitro method for identifying a substance of interest as having in-vivo androgen agonistic and androgen antagonistic properties, said method comprising the steps of:

obtaining a plurality of cells consisting of LNCaP.FGC (ATCC Accession No. CRL 1740) cultured in-vitro, said cells being androgen dependent for proliferation in-vivo;

maintaining a known quantity of said cultured cells in a maintaining medium without androgens, said maintaining medium comprising a fluid and an inhibitor of androgen dependent cell proliferation which is endogenous to the serum of humans or animals, said endogenous inhibitor being present in said maintaining medium at a concentration effective to prevent proliferation of said cells in-vitro in the absence of an androgen;

adding the substance of interest to a first aliquot of said cultured cells in said maintaining medium to form a first reaction mixture;

adding the substance of interest and an androgen to a second aliquot of said cultured cells in said maintaining medium to form a second reaction mixture;

incubating said first reaction mixture and said second reaction mixture for a preselected time period;

determining the number of cultured cells in said incubated first reaction mixture, a measurable increase in the number of cultured cells identifying the substance of interest as an androgen agonists and determining the number of cultured cells in said incubated second reaction mixture, the failure of said cultured cells to maximally increase in number identifying the substance of interest as an androgen antagonist.

4. The in-vitro method as recited in claim 1, 2, or 3 wherein said cultured cells comprise tumor cells derived from the prostate gland.

5. The in-vitro method as recited in claim 2 or 3 wherein said androgen is selected from the group consisting of testosterone, and 5α-dihydrotestosterone.

6. The in-vitro method as recited in claim 1, 2, or 3 wherein said maintaining medium comprises Dulbecco's modification of Eagle's Minimal Essential Medium.

7. The in-vitro method as recited in claim 1, 2, or 3 wherein said maintaining medium comprises charcoal-dextran stripped human serum.

8. The in-vitro method as recited in claim 1, 2, or 3 wherein said maintaining medium comprises charcoal-dextran stripped serum selected from the group consisting of bovine serum, horse serum, pig serum, mouse serum, and rat serum.

9. The in-vitro method as recited in claim 7 wherein said serum is used in a concentration ranging from 2% to 40% concentration by volume.

10. The in-vitro method as recited in claim 8 wherein said serum is used in a concentration ranging from 2% to 40% by volume.

11. The in-vitro method as recited in claim 1, 2, or 3 wherein said reaction mixtures are incubated for a time period ranging from 5 to 7 calendar days.

12. The in-vitro method as recited in claim 1, 2, or 3 wherein said maintaining medium comprises at least one selected from the group consisting of buffers vitamins, and salts.

* * * * *